US010465238B2

(12) United States Patent
Ji et al.

(10) Patent No.: US 10,465,238 B2
(45) Date of Patent: Nov. 5, 2019

(54) QUANTIFICATION OF MUTANT ALLELES AND COPY NUMBER VARIATION USING DIGITAL PCR WITH NONSPECIFIC DNA-BINDING DYES

(71) Applicant: The Board of Trustees of the Leland Stanford Junior University, Stanford, CA (US)

(72) Inventors: Hanlee P. Ji, Stanford, CA (US); Billy Tsz Cheong Lau, Palo Alto, CA (US); Laura Miotke, Omaha, NE (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 254 days.

(21) Appl. No.: 15/106,288

(22) PCT Filed: Dec. 16, 2014

(86) PCT No.: PCT/US2014/070657
§ 371 (c)(1),
(2) Date: Jun. 18, 2016

(87) PCT Pub. No.: WO2015/095225
PCT Pub. Date: Jun. 25, 2015

(65) Prior Publication Data
US 2016/0304936 A1 Oct. 20, 2016

Related U.S. Application Data

(60) Provisional application No. 61/918,633, filed on Dec. 19, 2013.

(51) Int. Cl.
| C12Q 1/68 | (2018.01) |
| C12P 19/34 | (2006.01) |
| C12Q 1/686 | (2018.01) |
| C12Q 1/6844 | (2018.01) |
| C12Q 1/6876 | (2018.01) |

(52) U.S. Cl.
CPC ............ *C12Q 1/686* (2013.01); *C12Q 1/6844* (2013.01); *C12Q 1/6876* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| 2006/0172324 A1* | 8/2006 | Wang .................... C12Q 1/6827 435/6.11 |
| 2013/0115601 A1 | 5/2013 | Bunce et al. |
| 2013/0136799 A1 | 5/2013 | Faham |
| 2013/0310269 A1* | 11/2013 | So ........................ C12Q 1/6853 506/9 |

FOREIGN PATENT DOCUMENTS

| WO | 2011/142836 A9 | 11/2011 |
| WO | 2013/181276 A1 | 12/2013 |

OTHER PUBLICATIONS

McDermott et al., "Multiplexed Target Detection Using DNA-Binding Dye Chemistry in Droplet Digital PCR," Analytical Chemistry, Nov. 3, vol. 85, pp. 11619-11627 (Year: 2013).*
Watanabe et al., "Determination of the HUMTH01 alleles by the APLP method," Int. J. Legal Med, vol. 112, pp. 134-135. (Year: 1999).*
Li et al., "BEAMing up for detection and quantification of rare sequence variants," Nature Methods, February, vol. 3, No. 2, pp. 95-97. (Year: 2006).*
Sykes et al. (1992) Quantitation of targets for PCR by use of limiting dilution. BioTechniques 13:444-449.
Vogelstein et al. (1999) Digital PCR. Proc. Natl. Acad. Sci. U.S.A. 96(16):9236-9241.
Ottesen et al. (2006) Microfluidic digital PCR enables multigene analysis of individual environmental bacteria. Science 314(5804):1464-1467.
Warren et al. (2006) Transcription factor profiling in individual hematopoietic progenitors by digital RT-PCR. Proc. Natl. Acad. Sci. U.S.A. 103(47):17807-17812.
Heyries et al. (2011) Megapixel digital PCR. Nat. Methods. 8(8):649-651.
Kiss et al. (2008) High-throughput quantitative polymerase chain reaction in picoliter droplets. Anal. Chem. 80(23):8975-8981.
Beer et al. (2008) On-chip single-copy real-time reverse-transcription PCR in isolated picoliter droplets. Anal. Chem. 80(6):1854-1858.
Shen et al. (2010) Digital PCR on a SlipChip. Lab Chip 10(20):2666-2672.
Hindson et al. (2011) High-throughput droplet digital PCR system for absolute quantitation of DNA copy number. Anal. Chem. 83(22):8604-8610.
Shen et al. (2011) Multiplexed quantification of nucleic acids with large dynamic range using multivolume digital RT-PCR on a rotational SlipChip tested with HIV and hepatitis C viral load. J. Am. Chem. Soc. 133(44):17705-17712.

(Continued)

*Primary Examiner* — Young J Kim
(74) *Attorney, Agent, or Firm* — Jenny L. Buchbinder; Bozicevic, Field & Francis LLP

(57) ABSTRACT

Methods and reagents for performing digital PCR for detection and quantification of mutant alleles and copy number variation are disclosed. In particular, the invention relates to methods using a nonspecific DNA-binding dye, which produces a fluorescent signal that increases in intensity according to the number of base-pairs present in the PCR amplicon product. The method utilizes mutant-specific and wild-type-specific primers having non-complementary "tail" sequences of different lengths. Accordingly, the amplicons for the wild-type and mutant alleles differ in length and can be distinguished based on the difference in the intensities of their fluorescent signals. The methods of the invention can be used to detect rare genetic events, including single nucleotide mutations, alterations of copy number, and deletions or insertions of nucleotides.

25 Claims, 13 Drawing Sheets

Specification includes a Sequence Listing.

(56) References Cited

OTHER PUBLICATIONS

Eischeid (2011) SYTO dyes and EvaGreen outperform Sybr Green in real-time PCR. BMC Res. Notes 4:263.
Mao et al. (2007) Characterization of EvaGreen and the implication of its physicochemical properties for qPCR applications. BMC Biotechnol. 7:76.
PCT/US2014/070657 International Search Report, dated Mar. 2015.

* cited by examiner

SEQUENCE LISTING

<160> NUMBER OF SEQ ID NOS: 25

<210> SEQ ID NO 1
<211> LENGTH: 21
<212> TYPE: DNA
<213> ORGANISM: Artificial Sequence
<220> FEATURE:
<223> OTHER INFORMATION: UC1 forward primer

<400> SEQUENCE: 1
tgagggattc ggcagatgtt g                                              21

<210> SEQ ID NO 2
<211> LENGTH: 22
<212> TYPE: DNA
<213> ORGANISM: Artificial Sequence
<220> FEATURE:
<223> OTHER INFORMATION: UC1 reverse primer

<400> SEQUENCE: 2
ctgaaaggct ggacttgaca ga                                             22

<210> SEQ ID NO 3
<211> LENGTH: 20
<212> TYPE: DNA
<213> ORGANISM: Artificial Sequence
<220> FEATURE:
<223> OTHER INFORMATION: FLT3 forward primer

<400> SEQUENCE: 3
gggataggac tcctgggttt                                                20

<210> SEQ ID NO 4
<211> LENGTH: 20
<212> TYPE: DNA
<213> ORGANISM: Artificial Sequence
<220> FEATURE:
<223> OTHER INFORMATION: FLT3 reverse primer

<400> SEQUENCE: 4
gtgagcagcc tgcattacct                                                20

-continued

```
<210> SEQ ID NO 5
<211> LENGTH: 20
<212> TYPE: DNA
<213> ORGANISM: Artificial Sequence
<220> FEATURE:
<223> OTHER INFORMATION: FLT3* forward primer

<400> SEQUENCE: 5
tcagtggcaa gaaacgacac                                                    20

<210> SEQ ID NO 6
<211> LENGTH: 20
<212> TYPE: DNA
<213> ORGANISM: Artificial Sequence
<220> FEATURE:
<223> OTHER INFORMATION: FLT3* reverse primer

<400> SEQUENCE: 6
agctgattga ctgggatgct                                                    20

<210> SEQ ID NO 7
<211> LENGTH: 20
<212> TYPE: DNA
<213> ORGANISM: Artificial Sequence
<220> FEATURE:
<223> OTHER INFORMATION: FLT3 forward primer

<400> SEQUENCE: 7
tcagtggcaa gaaacgacac                                                    20

<210> SEQ ID NO 8
<211> LENGTH: 20
<212> TYPE: DNA
<213> ORGANISM: Artificial Sequence
<220> FEATURE:
<223> OTHER INFORMATION: FLT3 reverse primer

<400> SEQUENCE: 8
gtgagcagcc tgcattacct                                                    20

<210> SEQ ID NO 9
<211> LENGTH: 20
<212> TYPE: DNA
<213> ORGANISM: Artificial Sequence
<220> FEATURE:
<223> OTHER INFORMATION: FLT3 forward primer

<400> SEQUENCE: 9
tcagtggcaa gaaacgacac                                                    20

<210> SEQ ID NO 10
<211> LENGTH: 20
<212> TYPE: DNA
<213> ORGANISM: Artificial Sequence
<220> FEATURE:
<223> OTHER INFORMATION: FLT3 reverse primer

<400> SEQUENCE: 10
attcaagcga gcctggttta                                                    20

<210> SEQ ID NO 11
<211> LENGTH: 20
<212> TYPE: DNA
<213> ORGANISM: Artificial Sequence
<220> FEATURE:
<223> OTHER INFORMATION: FLT3 forward primer
```

```
<400> SEQUENCE: 11
tcagtggcaa gaaacgacac                                              20

<210> SEQ ID NO 12
<211> LENGTH: 20
<212> TYPE: DNA
<213> ORGANISM: Artificial Sequence
<220> FEATURE:
<223> OTHER INFORMATION: FLT3 reverse primer

<400> SEQUENCE: 12
cagtgctcac tgccctaaca                                              20

<210> SEQ ID NO 13
<211> LENGTH: 20
<212> TYPE: DNA
<213> ORGANISM: Artificial Sequence
<220> FEATURE:
<223> OTHER INFORMATION: FLT3 forward primer

<400> SEQUENCE: 13
tcagtggcaa gaaacgacac                                              20

<210> SEQ ID NO 14
<211> LENGTH: 20
<212> TYPE: DNA
<213> ORGANISM: Artificial Sequence
<220> FEATURE:
<223> OTHER INFORMATION: FLT3 reverse primer

<400> SEQUENCE: 14
cattatggct gaacgctgtg                                              20

<210> SEQ ID NO 15
<211> LENGTH: 20
<212> TYPE: DNA
<213> ORGANISM: Artificial Sequence
<220> FEATURE:
<223> OTHER INFORMATION: FLT3 forward primer

<400> SEQUENCE: 15
tcagtggcaa gaaacgacac                                              20

<210> SEQ ID NO 16
<211> LENGTH: 21
<212> TYPE: DNA
<213> ORGANISM: Artificial Sequence
<220> FEATURE:
<223> OTHER INFORMATION: FLT3 reverse primer

<400> SEQUENCE: 16
cagcaccact cttccattga t                                            21

<210> SEQ ID NO 17
<211> LENGTH: 20
<212> TYPE: DNA
<213> ORGANISM: Artificial Sequence
<220> FEATURE:
<223> OTHER INFORMATION: FLT3 forward primer

<400> SEQUENCE: 17
tcagtggcaa gaaacgacac                                              20

<210> SEQ ID NO 18
<211> LENGTH: 21
```

```
<212> TYPE: DNA
<213> ORGANISM: Artificial Sequence
<220> FEATURE:
<223> OTHER INFORMATION: FLT3 reverse primer

<400> SEQUENCE: 18
ctgcaggtca ggttggataa t                                         21

<210> SEQ ID NO 19
<211> LENGTH: 20
<212> TYPE: DNA
<213> ORGANISM: Artificial Sequence
<220> FEATURE:
<223> OTHER INFORMATION: G6PD forward primer

<400> SEQUENCE: 19
gccagtggca gagtaaggag                                           20

<210> SEQ ID NO 20
<211> LENGTH: 20
<212> TYPE: DNA
<213> ORGANISM: Artificial Sequence
<220> FEATURE:
<223> OTHER INFORMATION: G6PD reverse primer

<400> SEQUENCE: 20
tctcctgggt ctcaggctta                                           20

<210> SEQ ID NO 21
<211> LENGTH: 20
<212> TYPE: DNA
<213> ORGANISM: Artificial Sequence
<220> FEATURE:
<223> OTHER INFORMATION: BRAF-WT forward primer

<400> SEQUENCE: 21
catgaagacc tcacagtaaa                                           20

<210> SEQ ID NO 22
<211> LENGTH: 19
<212> TYPE: DNA
<213> ORGANISM: Artificial Sequence
<220> FEATURE:
<223> OTHER INFORMATION: BRAF-WT reverse primer

<400> SEQUENCE: 22
ccactccatc gagatttca                                            19

<210> SEQ ID NO 23
<211> LENGTH: 20
<212> TYPE: DNA
<213> ORGANISM: Artificial Sequence
<220> FEATURE:
<223> OTHER INFORMATION: BRAF-MUT forward primer

<400> SEQUENCE: 23
catgaagacc tcacagtaaa                                           20

<210> SEQ ID NO 24
<211> LENGTH: 19
<212> TYPE: DNA
<213> ORGANISM: Artificial Sequence
<220> FEATURE:
<223> OTHER INFORMATION: BRAF-MUT reverse primer

<400> SEQUENCE: 24
```

```
ccactccatc gagatttct                                           19
```

<210> SEQ ID NO 25
<211> LENGTH: 39
<212> TYPE: DNA
<213> ORGANISM: Artificial Sequence
<220> FEATURE:
<223> OTHER INFORMATION: long 5'-tail

<400> SEQUENCE: 25

```
aaataaataa ataaataaat aaataaataa ataaataaa                     39
```

QUANTIFICATION OF MUTANT ALLELES AND COPY NUMBER VARIATION USING DIGITAL PCR WITH NONSPECIFIC DNA-BINDING DYES

STATEMENT REGARDING FEDERALLY SPONSORED RESEARCH OR DEVELOPMENT

This invention was made with Government support under contracts DK056339 and HG000205 awarded by the National Institutes of Health. The Government has certain rights in the invention.

TECHNICAL FIELD

The present invention pertains generally to digital polymerase chain reaction (PCR). In particular, the invention relates to methods of using dPCR with non-specific DNA binding dyes for detection and quantification of mutant alleles and copy number variation.

BACKGROUND

Digital PCR is a nucleic acid amplification and detection method that is based on the dilution of template DNA into independent non-interacting partitions (Sykes, et al. (1992) BioTechniques 13: 444-449). Following Poisson statistics with high dilutions of DNA template, each reaction is independently interrogated for the presence of a nucleic acid at single molecule sensitivity. Digital PCR was first implemented on high dilutions of template DNA into microtiter plates, but has recently matured through the use of microfabricated platforms (Vogelstein et al. (1999) Proc. Natl. Acad. Sci. U.S.A. 96(16):9236-9241; Ottesen et al. (2006) Science 314(5804):1464-1467; Warren et al. (2006) Proc. Natl. Acad. Sci. U.S.A. 103(47):17807-17812; Heyries et al. (2011) Nat. Methods. 8(8):649-651; Kiss et al. (2008) Anal. Chem. 80(23):8975-8981; Beer et al. (2008) Anal. Chem. 80(6):1854-1858; Shen et al. (2010) Lab Chip 10(20):2666-2672; and Hindson et al. (2011) Anal. Chem. 83(22):8604-8610). In recent years several companies have produced commercially accessible ways to automate and expand the range of partitioning. This included droplet digital PCR (ddPCR) systems (e.g. Bio-Rad QX200) that disperse template DNA randomly into emulsion droplets of equal volume (Hindson et al., supra).

Recently, digital PCR has seen wider use as an analytical tool for research and clinical applications. For example, digital PCR can be used as a robust tool for analyzing copy number variations seen in the amplifications or deletions of specific genes, detecting mutations, and quantifying specific nucleic acids species. Digital PCR has proven useful for identifying cancer genetic variation from tumors; frequently, these samples are admixtures between normal and tumor DNA.

Commonly, ddPCR platforms rely upon the use of fluorescently quenched oligonucleotide probes to hybridize to a region of interest. Upon PCR amplification, the 5' exonuclease activity of the polymerase separates the fluorophore from the quencher and generates a fluorescent signal specific to the target. The fluorescence of these partitions can be individually measured after amplification in order to determine the presence or absence of template molecules. The use of different fluorescent dyes allows for the simultaneous normalization of one genomic DNA region of interest (ROI) against a reference amplicon in a single reaction. However, the major limitation of using fluorescent oligonucleotide probes in digital copy number analysis is the scalability of synthesis and optimization for a large number of genes.

Recent studies have explored the application of DNA binding dyes such as EvaGreen (EG) for the quantitation of single amplicons in a digital PCR format (Shen et al., supra; Shen et al. (2011) J. Am. Chem. Soc. 133(44):17705-17712). The EG fluorophore is a non-specific double-stranded DNA (dsDNA) binding dye. When no DNA is present, EG assumes an inactive configuration, emitting a fluorescent signal only when template is bound. The method of binding allows for the use of a higher concentration without inhibiting PCR and thus maintaining a higher resolution signal compared to SYBR dye (Eischeid (2011) BMC Res. Notes 4:263). The EG-DNA complex produces a maximum amplitude fluorescent signal at an excitation wavelength of 500 nm and an emission wavelength of 530 nm (Mao et al. (2007) BMC Biotechnol. 7:76). In comparison, digital PCR systems utilizing fluorescent oligonucleotide probes commonly consist of multiple spectrally distinct fluorophores for the detection of different targets. As only one wavelength can be used in an EG-based digital PCR format to detect both the reference and ROI, new multiplexing strategies independent of spectral context must be developed.

Thus, there remains a need for the development of efficient, effective strategies for performing digital PCR analysis.

SUMMARY

The present invention relates to methods and reagents for performing digital PCR for detection and quantification of mutant alleles and copy number variation. In particular, the invention relates to methods using a nonspecific DNA-binding dye, which produces a fluorescent signal that increases in intensity according to the number of base-pairs present in the PCR amplicon product. The method utilizes mutant-specific and wild-type-specific primers having non-complementary "tail" sequences of different lengths. Accordingly, the amplicons for the wild-type and mutant alleles differ in length and can be distinguished based on the difference in the intensities of their fluorescent signals. The methods of the invention can be used to detect rare genetic events, including single nucleotide mutations, alterations of copy number, and deletions or insertions of nucleotides.

In one aspect, the invention includes a composition for performing digital PCR, the composition comprising: a) a first set of primers for amplification of a region of interest in a target polynucleotide sequence, wherein each primer comprises a 5'-tail of a first length; b) a second set of primers for amplification of a reference polynucleotide sequence, wherein each primer comprises a 5'-tail of a second length, such that amplifying nucleic acids with the primers will result in amplicons of the region of interest and amplicons of the reference polynucleotide sequence having different lengths; and c) a fluorescent DNA dye. The fluorescent DNA dye can be any dye that binds nonspecifically to DNA (i.e. binds DNA of any sequence) that will allow discrimination of amplicons by length and quantitative measurement of target nucleic acids. Dyes that can be used in the practice of the invention include, but are not limited to EvaGreen dye (EG) dye, SYBR green, SYBR green II, SYBR gold, Oxazole yellow (YO), YOYO, Thiazole orange (TO), PicoGreen (PG), and SYTO dyes. The composition may further comprise reagents for performing droplet digital PCR.

In one embodiment, the region of interest in the target polynucleotide comprises a mutation and the reference polynucleotide sequence comprises a wild-type sequence. The mutation may include a replacement, an insertion, or a deletion. The mutation can be a common genetic variant or a rare genetic variant. In one embodiment, the mutation is a single nucleotide variation. In one embodiment, the target polynucleotide sequence is a sequence for which deletion or duplication is associated with a phenotype of interest. The region of interest may comprise a sequence known to exhibit genomic copy number variation. For example, 1, 2, 3, 4, 5, or 6 or more copies of the target polynucleotide sequence may be present in the genome of a subject.

In another aspect, the invention includes a method for determining the relative copy number of a target polynucleotide sequence in a genome of a subject, the method comprising: a) collecting a biological sample comprising nucleic acids from the subject; b) dividing the nucleic acids of the biological sample into a plurality of partitions; c) amplifying the nucleic acids by digital PCR using a composition for performing digital PCR as described herein, wherein the size of the amplicons for the target polynucleotide sequence and the reference polynucleotide sequence differ in length; d) measuring the fluorescence signal from each partition after amplification in order to determine the presence or absence of amplicons for the region of interest of the target polynucleotide and the reference polynucleotide sequence; and e) summing the results over all the partitions to determine the relative copy number of the target polynucleotide sequence compared to the reference polynucleotide sequence. In one embodiment, at least one primer hybridizes to a coding region of the target polynucleotide. In another embodiment, at least one primer hybridizes to a non-coding region of the target polynucleotide.

In another aspect, the invention includes a method for detecting and quantifying a mutation in a target polynucleotide sequence in a genome of a subject, the method comprising: a) collecting a biological sample comprising nucleic acids from the subject; b) dividing the nucleic acids of the biological sample into a plurality of partitions; c) amplifying the nucleic acids by digital PCR using a composition for performing digital PCR, as described herein, to produce an amplicon of the region of interest comprising the mutation, wherein the amplicon of the region of interest differs in length from the amplicon of a reference polynucleotide sequence comprising a non-variant reference sequence for the target polynucleotide; d) measuring the fluorescence signal from each partition after amplification in order to determine the presence or absence of amplicons for the region of interest and the non-variant reference sequence; and e) summing the results over all the partitions to determine the relative amount of the mutation in the genome of the subject compared to the non-variant reference sequence. The method may further comprise isolating at least one target polynucleotide from the biological sample.

In certain embodiments, the mutation is a nucleotide insertion, deletion, or replacement. In one embodiment, the mutation is a single nucleotide variation. The mutation can be a common genetic variant or a rare genetic variant. In one embodiment, the mutation is associated with a phenotype (e.g., disease or condition) of interest.

The methods of the invention can be used to analyze nucleic acids from biological samples, including cells, tissue, or fluid isolated from any prokaryotic or eukaryotic organism, such as animals, plants, bacteria, fungi, or protists. In certain embodiments, the biological sample comprises a genetically aberrant cell, rare blood cell, or cancerous cell. In particular, the methods of the invention can be used to analyze genetic variation in tumors, including mutations and copy number variation associated with cancer progression.

In one embodiment, digital PCR is performed, as described herein, in a microfluidic device.

In another aspect, the invention includes a kit for performing digital PCR. The kit may comprise a composition comprising primers and a fluorescent DNA dye, as described herein, for performing digital PCR. The kit may further comprise written instructions for performing digital PCR and analyzing nucleic acids for mutant alleles or copy number variation. The kit may also comprise a polymerase, nucleotides, buffers and other reagents for performing digital PCR. In one embodiment, the kit further comprises reagents for performing droplet digital PCR.

These and other embodiments of the subject invention will readily occur to those of skill in the art in view of the disclosure herein.

BRIEF DESCRIPTION OF THE DRAWINGS

FIG. 2A shows reverse primers, which were designed to flank increasing length regions of FLT3 with a common forward primer. All primers were approximately 20 bp. FIG. 2B shows each column representing individual wells of about 20,000 droplets with a single set of FLT3 primers. Amplicons greater than 500 bp were allowed to anneal/extend for two minutes instead of one.

FIG. 3A shows NA18507 control genomic DNA, which served as a template for simplex PCR amplification of FLT3 (66 bp), UC1 (60 bp), and a multiplexed reaction for both targets. Amplicons were run on a SybrGold PAGE gel. FIG. 3B shows each column representing a single well of about 20,000 droplets containing NA18507 template with multiplexed UC1 and FLT3.

FIG. 4B shows FLT3 copy number as measured in a serial dilution of NCIH176 colorectal cancer cell line into a normal diploid human control, NA18507 (Coriell). The expected copy number (dark gray) was calculated from the Cancer Cell Line Encyclopedia (Broad) data on copy number derived from microarray.

FIGS. 5A and 5B show primers designed with the single nucleotide variant at the 3' end of the complementary region. Noncomplementary tails of varying lengths are then added to the 5' end and amplified with a universal reverse primer. FIG. 5C shows a 1:4 mixture of MUT:WT BRAF template amplified with mutant primers with the short tail and wild-type primers with the long tail. FIG. 5D shows a swap: 1:4 mixture of MUT:WT BRAF template amplified with wild-type primers with the short tail and mutant primers with the long tail. FIG. 5E shows a serial dilution of mutant BRAF template (LS411N) into wild-type (Human male control). Theoretical % mutant was calculated from TaqMan measured concentrations of mutant and wild-type template. The assay was performed with the EvaGreen primer mix from FIG. 5C. FIG. 5F shows a close-up of three data points on the lower end of the dilution series from FIG. 5E.

DETAILED DESCRIPTION OF THE INVENTION

Figure 1:
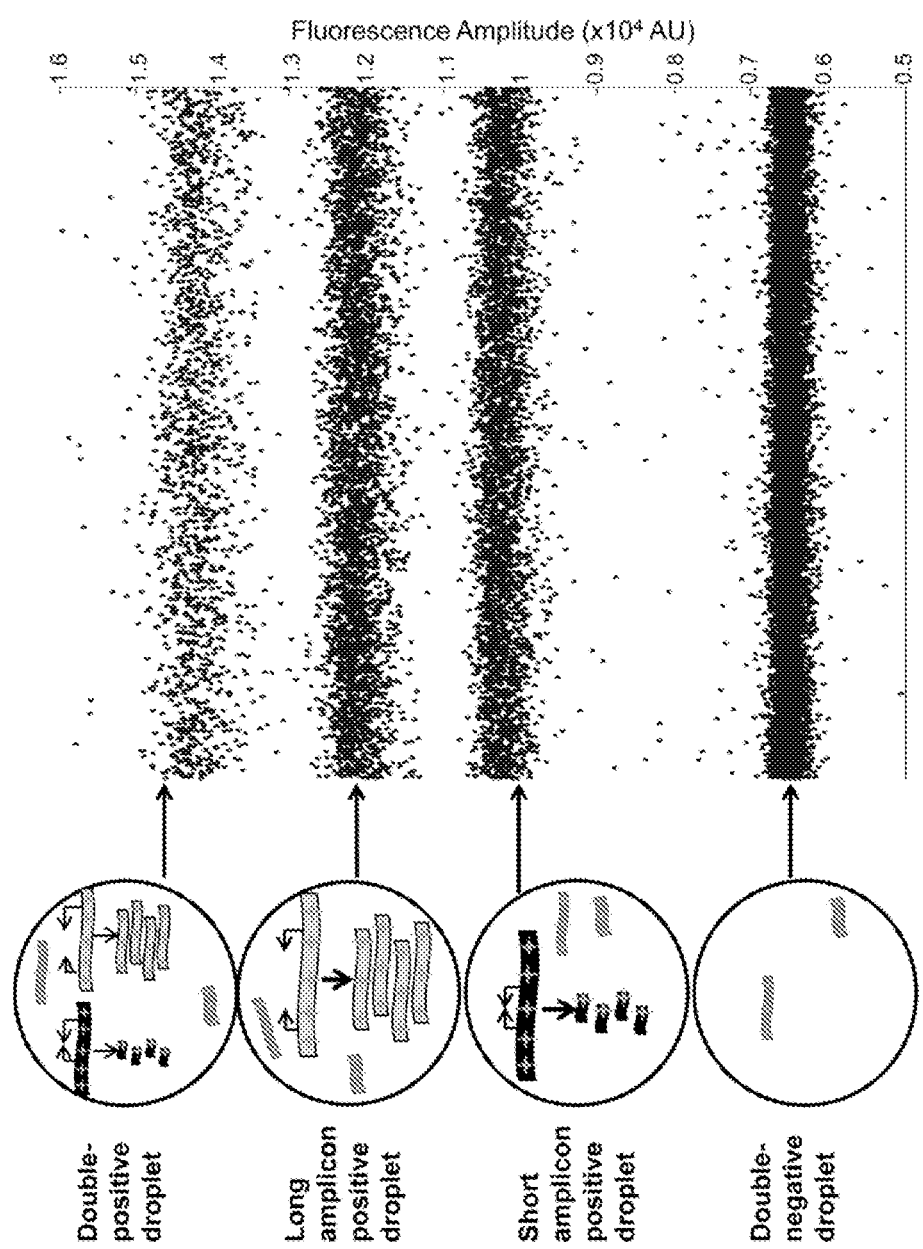
FIG. 1 shows a schematic of droplet-digital PCR with EvaGreen Dye. Droplets are formed pre-PCR by randomly sequestering fragmented template DNA into equal volume partitions. The first population of droplets corresponds with the lowest fluorescent amplitude have only the unamplified background template DNA (gray). The second population represents the droplets containing only the short amplicon template (black). For copy number variation (CNV) analysis this is UC1 (60 bp) and for single nucleotide variation (SNV) analysis this is the short-tail amplicon (71 bp). The third population represents droplets with only the long amplicon template (gray). For CNV analysis this is the ROI (66 bp) and for SNV analysis this is the long-tail amplicon (104 bp). The population with the highest amplitude represents droplets containing both amplified targets.

The practice of the present invention will employ, unless otherwise indicated, conventional methods of chemistry, biochemistry, molecular biology and recombinant DNA techniques, within the skill of the art. Such techniques are explained fully in the literature. See, e.g., T. Nolan and S. A. Bustin *PCR Technology: Current Innovations* (CRC Press, 3$^{rd}$ edition, 2013); S. A. Bustin *A-Z of Quantitative PCR* (International University Line, 2004); E. van Pelt-Verkuil, A. van Belkum, J. P. Hays *Principles and Technical Aspects of PCR Amplification* (Springer, 2008); T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (3$^{rd}$ Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

1. DEFINITIONS

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a polynucleotide" includes a mixture of two or more such polynucleotides, and the like.

The term "common genetic variant" or "common variant" refers to a genetic variant having a minor allele frequency (MAF) of greater than 5%.

The term "rare genetic variant" or "rare variant" refers to a genetic variant having a minor allele frequency (MAF) of less than or equal to 5%.

The term "rare blood cell" refers to a type of cell found in blood in an amount of less than 100 cells/ml of whole blood.

"Substantially purified" generally refers to isolation of a substance (compound, polynucleotide, oligonucleotide, protein, or polypeptide) such that the substance comprises the majority percent of the sample in which it resides. Typically in a sample, a substantially purified component comprises 50%, preferably 80%-85%, more preferably 90-95% of the sample. Techniques for purifying polynucleotides, oligonucleotides, and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide or oligonucleotide is a nucleic acid molecule devoid, in whole or part, of sequences normally associated with it in nature; or a sequence, as it exists in nature, but having heterologous sequences in association therewith; or a molecule disassociated from the chromosome.

"Homology" refers to the percent identity between two polynucleotide or two polypeptide moieties. Two nucleic acid, or two polypeptide sequences are "substantially homologous" to each other when the sequences exhibit at least about 50% sequence identity, preferably at least about 75% sequence identity, more preferably at least about 80%-85% sequence identity, more preferably at least about 90% sequence identity, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

As used herein, a "solid support" refers to a solid surface such as a magnetic bead, latex bead, microtiter plate well, glass plate, nylon, agarose, acrylamide, and the like.

As used herein, the term "target DNA," "target polynucleotide," or "target nucleic acid" denotes a nucleic acid molecule (e.g., comprising a region of interest) with a "target sequence" that hybridizes to a primer and can be detected and quantified by digital PCR analysis. The target nucleic acid may include other sequences besides the target sequence, which hybridizes to a primer, including adapter sequences to facilitate high-throughput sequencing or amplification.

The term "primer" or "oligonucleotide primer" as used herein, refers to an oligonucleotide that hybridizes to the template strand of a nucleic acid and initiates synthesis of a nucleic acid strand complementary to the template strand when placed under conditions in which synthesis of a primer extension product is induced, i.e., in the presence of nucleotides and a polymerization-inducing agent such as a DNA or RNA polymerase and at suitable temperature, pH, metal concentration, and salt concentration. The primer is preferably single-stranded for maximum efficiency in amplification, but may alternatively be double-stranded. If double-stranded, the primer can first be treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA or RNA synthesis. A primer need not reflect the exact sequence of the template but must be sufficiently complementary to hybridize with a template. A primer may further comprise a "tail" comprising additional nucleotides at the 5' end of the primer that are non-complementary to the template. Typically, the lengths of primers range between 7-100 nucleotides in length, such as 15-60, 20-40, and so on, more typically in the range of between 20-40 nucleotides in length, and any length between the stated ranges. Shorter primer molecules generally require cooler temperatures to form sufficiently stable hybrid complexes with the template. The term "primer site" or "primer binding site" refers to the segment of the target DNA to which a primer hybridizes. Typically, a set of primers is used for amplification of a target polynucleotide, including a 5' "upstream primer" or "forward primer" that hybridizes with the complement of the 5' end of the DNA sequence to be amplified and a 3' "downstream primer" or "reverse primer" that hybridizes with the 3' end of the sequence to be amplified.

The term "amplicon" refers to the amplified nucleic acid product of a PCR reaction or other nucleic acid amplification process (e.g., ligase chain reaction (LGR), nucleic acid sequence based amplification (NASBA), transcription-mediated amplification (TMA), Q-beta amplification, strand displacement amplification, or target mediated amplification).

As used herein, the term "probe" or "oligonucleotide probe" refers to a polynucleotide, as defined above, that contains a nucleic acid sequence complementary to a nucleic acid sequence present in the target nucleic acid analyte. The polynucleotide regions of probes may be composed of DNA, and/or RNA, and/or synthetic nucleotide analogs. Probes may be labeled in order to detect the target sequence. Such a label may be present at the 5' end, at the 3' end, at both the 5' and 3' ends, and/or internally. Additionally, the oligonucleotide probe will typically be derived from a sequence that lies between the sense and the antisense primers when used in a nucleic acid amplification assay.

It will be appreciated that the hybridizing sequences need not have perfect complementarity to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

The "melting temperature" or "Tm" of double-stranded DNA is defined as the temperature at which half of the helical structure of DNA is lost due to heating or other dissociation of the hydrogen bonding between base pairs, for example, by acid or alkali treatment, or the like. The $T_m$ of a DNA molecule depends on its length and on its base composition. DNA molecules rich in GC base pairs have a higher $T_m$ than those having an abundance of AT base pairs. Separated complementary strands of DNA spontaneously reassociate or anneal to form duplex DNA when the temperature is lowered below the $T_m$. The highest rate of nucleic acid hybridization occurs approximately 25 degrees C. below the $T_m$. The $T_m$ may be estimated using the following relationship: $T_m$=69.3+0.41 (GC) % (Marmur et al. (1962) *J. Mol. Biol.* 5:109-118).

As used herein, a "biological sample" refers to a sample of cells, tissue, or fluid isolated from a prokaryotic or eukaryotic organism, including but not limited to, for example, blood, plasma, serum, fecal matter, urine, bone marrow, bile, spinal fluid, lymph fluid, sputum, ascites, bronchial lavage fluid, synovial fluid, samples of the skin, external secretions of the skin, respiratory, intestinal, and genitourinary tracts, tears, saliva, milk, organs, biopsies, and also samples of cells, including cells from bacteria, fungi, protists, plants, and animals as well as in vitro cell culture constituents, including but not limited to, conditioned media resulting from the growth of cells and tissues in culture medium, e.g., recombinant cells, and cell components, and also samples containing nucleic acids from viruses.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, semiconductor nanoparticles, dyes, metal ions, metal sols, ligands (e.g., biotin, strepavidin or haptens) and the like. The term "fluorescer" refers to a substance or a portion thereof which is capable of exhibiting fluorescence in the detectable range. Particular examples of labels which may be used in the practice of the invention include, but are not limited to, EvaGreen dye (EG) dye, SYBR green, SYBR green II, SYBR gold, SYTO dye, Oxazole yellow (YO), YOYO, Thiazole orange (TO), PicoGreen (PG), fluorescein, carboxyfluorescein (FAM), CAL Fluor Orange 560, CAL Fluor Red 610, Quasar Blue 670, tetramethyl rhodamine (TAMRA), 2',4',5',7'-tetrachloro-4-7-dichlorofluorescein (TET), FITC, rhodamine, dansyl, umbelliferone, dimethyl acridinium ester (DMAE), Texas red, luminol, NADPH, horseradish peroxidase (HRP), and α-β-galactosidase.

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; birds; and laboratory animals, including rodents such as mice, rats and guinea pigs, and the like. The term does not denote a particular age. Thus, both adult and newborn individuals are intended to be covered.

2. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of reagents and methods for performing digital PCR for detection and quantification of mutant alleles and copy number variation. In particular, the methods utilize a nonspecific DNA-binding dye, which produces a fluorescent signal that increases in intensity according to the number of base-pairs present in a PCR amplicon product. Mutant-specific and wild-type-specific primers are designed having non-complementary "tail" sequences that differ in length. Accordingly, the resulting amplicons for the wild-type and mutant alleles differ in length and can be distinguished based on the difference in the intensities of their fluorescent signals (see Example 1).

In order to further an understanding of the invention, a more detailed discussion is provided below regarding reagents and methods for performing digital PCR.

A. Digital PCR with a Nonspecific DNA Dye

The invention includes methods and reagents, including specially designed primers for performing PCR with use of a nonspecific DNA dye, in particular, for detection and quantification of mutant alleles and copy number variation. The methods of the invention utilize at least two sets of primers for separately amplifying a region of interest in a target polynucleotide sequence and a reference polynucleotide sequence used for comparison. Primers are designed with a 5' tail sequence to allow discrimination of amplicons for the target polynucleotide and the reference polynucleotide. A first set of primers having tails of a certain length is used for amplification of the region of interest in the target polynucleotide sequence, and a second set of primers having tails of a different length from that of the first set of primers is used for amplification of the reference polynucleotide sequence, such that amplifying the nucleic acids with the two sets of primers results in amplicons of the target polynucleotide and the reference polynucleotide having detectably different lengths.

A fluorescent DNA dye is used for detection of the amplicons resulting from the PCR reaction. Any DNA dye can be used that binds nonspecifically to DNA (i.e. binds DNA of any sequence), which permits discrimination of the amplicons by length and quantitative measurement of the nucleic acids. Exemplary DNA dyes that can be used include EvaGreen dye (EG) dye, SYBR green, SYBR green II, SYBR gold, Oxazole yellow (YO), YOYO, Thiazole orange (TO), PicoGreen (PG), and SYTO dyes.

Primers are designed with a region that is complementary to a portion of the template nucleic acid to be amplified to allow initiation of the polymerization reaction. Noncomplementary nucleotides are added to the 5' ends of primers to create the 5' tails. Typically, the lengths of primers range between 7-100 nucleotides in length, such as 15-60, 20-40, and so on, more typically in the range of between 20-40 nucleotides long, and any length between the stated ranges.

It is desirable that the amplification efficiencies of the target and reference sequences be similar or approximately equal, in order to allow comparison for quantitative analyses. For this reason, primers and amplification conditions should be selected to obtain this result. For example, the lengths of the primers can be extended or shortened at the 5' end or the 3' end to produce primers with desired melting temperatures. Although the complimentary regions of primers designed for amplification of the target and reference sequences may be the same length, their non-complimentary tail sequences will generally have different lengths to allow discrimination of amplicons for the target and reference polynucleotides. Primers with shorter tails can be designed with a higher GC content, whereas primers with longer tails can be designed with a higher AT content to approximately match melting temperatures for the primer-template complexes for target and reference polynucleotides, preferably within 3° C. of each other. The amplification efficiency of any pair of primers can be readily determined using routine techniques (see e.g., Furtado et al., "Application of real-time quantitative PCR in the analysis of gene expression." DNA amplification: Current Technologies and Applications. Wymondham, Norfolk, UK: Horizon Bioscience p. 131-145 (2004)).

Primers can readily be synthesized by standard techniques, e.g., solid phase synthesis via phosphoramidite chemistry, as disclosed in U.S. Pat. Nos. 4,458,066 and 4,415,732, incorporated herein by reference; Beaucage et al., *Tetrahedron* (1992) 48:2223-2311; and Applied Biosystems User Bulletin No. 13 (1 Apr. 1987). Other chemical synthesis methods include, for example, the phosphotriester method described by Narang et al., *Meth. Enzymol.* (1979) 68:90 and the phosphodiester method disclosed by Brown et al., *Meth. Enzymol.* (1979) 68:109. Poly(A) or poly(C), or other non-complementary nucleotide extensions may be incorporated into oligonucleotides using these same methods. Hexaethylene oxide extensions may be coupled to the oligonucleotides by methods known in the art. Cload et al., *J. Am. Chem. Soc.* (1991) 113:6324-6326; U.S. Pat. No. 4,914,210 to Levenson et al.; Durand et al., *Nucleic Acids Res.* (1990) 18:6353-6359; and Horn et al., *Tet. Lett.* (1986) 27:4705-4708.

In addition, one or more PCR additives or enhancing agents may be included to improve the yield of the amplification reaction, for example, by reducing secondary structure in a nucleic acid or mispriming events. Such additives or enhancing agents include, but are not limited to, dimethyl sulfoxide (DMSO), N,N,N-trimethylglycine (betaine), formamide, glycerol, nonionic detergents (e.g., Triton X-100, Tween 20, and Nonidet P-40 (NP-40)), 7-deaza-2'-deoxyguanosine, bovine serum albumin, T4 gene 32 protein, polyethylene glycol, 1,2-propanediol, and tetramethylammonium chloride.

The biological sample containing nucleic acids to be analyzed can be any sample of cells, tissue, or fluid isolated from a prokaryotic or eukaryotic organism, including but not limited to, for example, blood, plasma, serum, fecal matter, urine, bone marrow, bile, spinal fluid, lymph fluid, sputum, ascites, bronchial lavage fluid, synovial fluid, samples of the skin, external secretions of the skin, respiratory, intestinal, and genitourinary tracts, tears, saliva, milk, organs, biopsies, and also samples of cells, including cells from bacteria, fungi, protists, plants, and animals as well as in vitro cell culture constituents, including but not limited to, conditioned media resulting from the growth of cells and tissues in culture medium, e.g., recombinant cells, and cell components, and also samples containing nucleic acids from viruses. In certain embodiments, the biological sample comprises a genetically aberrant cell, rare blood cell, or cancerous cell.

The biological sample may be pre-treated in any number of ways prior to performance of PCR. Preparation of the sample may include any suitable manipulation of the sample, such as collection, dilution, concentration, purification, lyophilization, freezing, extraction, combination with one or more assay reagents, or any combination thereof. For instance, in certain embodiments, the sample may be treated to disrupt or lyse cells or viral particles, for example by treating the samples with one or more detergents and/or denaturing agents (e.g., guanidinium agents). Nucleic acids may also be extracted from samples, for example, after detergent treatment and/or denaturing as described above. Total nucleic acid extraction may be performed using known techniques, for example by non-specific binding to a solid phase (e.g., silica). See, e.g., U.S. Pat. Nos. 5,234,809; 6,849,431; 6,838,243; 6,815,541; and 6,720,166. In some embodiments, preparation of the sample may include combining the sample with reagents for amplification and for reporting whether or not amplification has occurred. Reagents for amplification may include any combination of primers for the target polynucleotides, deoxynucleoside triphosphates (dNTPs) and/or nucleoside triphosphates (NTPs), at least one enzyme (e.g., a polymerase, a ligase, a reverse transcriptase, or a combination thereof, each of which may or may not be heat-stable), and/or the like. Accordingly, preparation of the sample may render the sample (or partitions thereof) capable of amplification of each of one or more target polynucleotides, if present, in the sample (or a partition thereof).

The target polynucleotide may be any nucleic acid of interest. Target polynucleotides may include naturally occurring genomic DNA or RNA or genetically altered or synthetically prepared nucleic acids and may be obtained from virtually any source, including plants, animals, bacteria, fungi, and protists. The target polynucleotide may also include cDNA generated from RNA (e.g., mRNA, non-coding RNA, microRNA, siRNA, ribosomal RNA, tRNA, catalytic RNA, or viral RNA) by reverse transcription.

As explained above, primers designed with 5'-tails may be used in polymerase chain reaction (PCR)-based techniques to distinguish amplicons resulting from different polynucleotide sequences based on length. PCR can be used for amplifying a desired target nucleic acid sequence contained in a nucleic acid molecule or mixture of molecules. In PCR, a pair of primers is employed in excess to hybridize to the complementary strands of the target nucleic acid. The primers are each extended by a polymerase using the target nucleic acid as a template. The extension products become target sequences themselves after dissociation from the original target strand. New primers are then hybridized and extended by a polymerase, and the cycle is repeated to geometrically increase the number of target sequence molecules. The PCR method for amplifying target nucleic acid sequences in a sample is well known in the art and has been described in, e.g., Innis et al. (eds.) *PCR Protocols* (Academic Press, NY 1990); Taylor (1991) *Polymerase chain reaction: basic principles and automation*, in *PCR: A Practical Approach*, McPherson et al. (eds.) IRL Press, Oxford; Saiki et al. (1986) *Nature* 324:163; as well as in U.S. Pat. Nos. 4,683,195, 4,683,202 and 4,889,818, all incorporated herein by reference in their entireties.

In particular, PCR uses relatively short oligonucleotide primers which flank the target nucleotide sequence to be amplified, oriented such that their 3' ends face each other, each primer extending toward the other. The polynucleotide sample is extracted and denatured, preferably by heat, and hybridized with the first and second primers that are present in molar excess. Polymerization is catalyzed in the presence of the four deoxyribonucleotide triphosphates (dNTPs—dATP, dGTP, dCTP and dTTP) using a primer- and template-dependent polynucleotide polymerizing agent, such as any enzyme capable of producing primer extension products, for example, *E. coli* DNA polymerase I, Klenow fragment of DNA polymerase I, T4 DNA polymerase, thermostable DNA polymerases isolated from *Thermus aquaticus* (Taq), available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs). This results in two "long products" which contain the respective primers at their 5' ends covalently linked to the newly synthesized complements of the original strands. The reaction mixture is then returned to polymerizing conditions, e.g., by lowering the temperature, inactivating a denaturing agent, or adding more polymerase, and a second cycle is initiated. The second cycle provides the two original strands, the two long products from the first cycle, two new long products replicated from the original strands, and two "short products" replicated from the long products. The short products have the sequence of the target sequence with a primer at each end. On each additional cycle, an additional two long products are produced, and a number of short products equal to the number of long and short products remaining at the end of the previous cycle. Thus, the number of short products containing the target sequence grows exponentially with each cycle. Preferably, PCR is carried out with a commercially available thermal cycler, e.g., Perkin Elmer. The amplification products can be detected in solution or using solid supports.

RNAs may be amplified by reverse transcribing the RNA into cDNA, and then performing PCR (RT-PCR), as described above. Alternatively, a single enzyme may be used for both steps as described in U.S. Pat. No. 5,322,770, incorporated herein by reference in its entirety. RNA may also be reverse transcribed into cDNA, followed by asymmetric gap ligase chain reaction (RT-AGLCR) as described by Marshall et al. (1994) *PCR Meth. App.* 4:80-84.

In particular, the methods of the invention are applicable to digital PCR methods. For digital PCR, a sample containing nucleic acids is separated into a large number of partitions before performing PCR. Partitioning can be achieved in a variety of ways known in the art, for example, by use of micro well plates, capillaries, emulsions, arrays of miniaturized chambers or nucleic acid binding surfaces. Separation of the sample may involve distributing any suitable portion including up to the entire sample among the partitions. Each partition includes a fluid volume that is isolated from the fluid volumes of other partitions. The partitions may be isolated from one another by a fluid phase, such as a continuous phase of an emulsion, by a solid phase, such as at least one wall of a container, or a combination thereof. In certain embodiments, the partitions may comprise droplets disposed in a continuous phase, such that the droplets and the continuous phase collectively form an emulsion.

The partitions may be formed by any suitable procedure, in any suitable manner, and with any suitable properties. For example, the partitions may be formed with a fluid dispenser, such as a pipette, with a droplet generator, by agitation of the sample (e.g., shaking, stirring, sonication, etc.), and the like. Accordingly, the partitions may be formed serially, in parallel, or in batch. The partitions may have any suitable volume or volumes. The partitions may be of substantially uniform volume or may have different volumes. Exemplary partitions having substantially the same volume are monodisperse droplets. Exemplary volumes for the partitions include an average volume of less than about 100, 10 or 1 µL, less than about 100, 10, or 1 nL, or less than about 100, 10, or 1 pL, among others.

After separation of the sample, PCR is carried out in the partitions. The partitions, when formed, may be competent for performance of one or more reactions in the partitions. Alternatively, one or more reagents may be added to the partitions after they are formed to render them competent for reaction. The reagents may be added by any suitable mechanism, such as a fluid dispenser, fusion of droplets, or the like.

After PCR amplification, nucleic acids are quantified by counting the partitions that contain PCR amplicons for the target and/or reference polynucleotides. Partitioning of the sample allows quantification of the number of different molecules by assuming that the population of molecules follows a Poisson distribution. For a description of digital PCR methods, see, e.g., Hindson et al. (2011) Anal. Chem.

83(22):8604-8610; Pohl and Shih (2004) Expert Rev. Mol. Diagn. 4(1):41-47; Pekin et al. (2011) Lab Chip 11 (13): 2156-2166; Pinheiro et al. (2012) Anal. Chem. 84 (2): 1003-1011; Day et al. (2013) Methods 59(1):101-107; herein incorporated by reference in their entireties.

B. Applications

The methods of the invention can be used to detect common or rare genetic events, such as mutations (e.g., nucleotide replacements, insertions, or deletions) and alterations of copy number. Mutations can be common genetic variants or rare genetic variants and may include single nucleotide variants. In certain embodiments, the target sequence is a sequence for which mutation, deletion or duplication is associated with a phenotype of interest (e.g., disease or condition). In other embodiments, the target sequence is a sequence for which mutation, deletion or duplication is not associated with a known phenotype of interest, but for which information about the distribution or correlation of the variation in a particular population is desired. In particular, the methods of the invention can be used to analyze genetic variation in tumors, including mutations and copy number variation associated with cancer progression.

The region of interest may comprise a sequence known to exhibit genomic copy number variation. For example, 1, 2, 3, 4, 5, or 6 or more copies of the target polynucleotide sequence may be present in the genome of a subject. Copy number variation can be calculated based on "relative copy number" so that apparent differences in gene copy numbers in different samples are not distorted by differences in sample amounts. The relative copy number of a gene (per genome) can be expressed as the ratio of the copy number of a target gene to the copy number of a reference polynucleotide sequence in a DNA sample. The reference polynucleotide sequence can be a sequence having a known genomic copy number. Typically the reference sequence will have a single genomic copy and is a sequence that is not likely to be amplified or deleted in the genome. It is not necessary to empirically determine the copy number of a reference sequence in each assay. Rather, the copy number may be assumed based on the normal copy number in the organism of interest. By selecting tail lengths for the target polynucleotide sequence and the reference polynucleotide sequence that allow discrimination of their amplicons, both genes in the same DNA sample can be quantitated simultaneously. Accordingly, the relative copy number of the target nucleotide sequence in a DNA sample is calculated from the ratio of the two genes.

The methods of the invention can be adapted for multiplex PCR, for example, to detect and/or quantify multiple target polynucleotides simultaneously. Thus, a plurality of primer sets, comprising forward and reverse primers, can be used in each reaction mixture, each set of primers directed to different target polynucleotide sequences and comprising 5' tails of detectably different lengths to allow the amplicons produced from the different target polynucleotides to be distinguished based on the intensity of their fluorescent signals after binding a nonspecific fluorescent DNA dye. In some cases, multiplexing is performed such that all species of various target polynucleotides of interest can be simultaneously detected and/or quantified from a single sample. In certain embodiments, a plurality of primers sets is used to simultaneously detect and/quantify different target alleles at the same locus or at different target loci. In other embodiments, a plurality of primers sets is used to simultaneously quantify copy number variation of different target polynucleotide sequences.

C. Kits

The above-described assay reagents, including primers and nonspecific fluorescent DNA dyes for performing PCR, can be provided in kits, with suitable instructions and other necessary reagents, in order to detect and/or quantify target polynucleotide sequences, including, in particular, mutant alleles and copy number variation as described above. The kit will normally contain in separate containers the primers, DNA dyes, and other reagents required for PCR. Instructions (e.g., written, CD-ROM, DVD, flash drive, SD card, etc.) for carrying out PCR and quantification of mutant alleles and copy number variation usually will be included in the kit. The kit may also contain other packaged reagents and materials (i.e., wash buffers, control formulations (positive and/or negative), reagents and/or devices for performing digital PCR, and the like). PCR assays, such as those described herein, can be conducted using these kits.

3. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

High Sensitivity Detection and Quantitation of DNA Copy Number and Single Nucleotide Variants with Single Color Digital Droplet PCR In this study we present a highly customizable method for quantifying copy number and point mutations utilizing a single-color, droplet-digital PCR platform. To achieve a multiplexed format in a single-color system, we took advantage of the varying amplitudes of EvaGreen dye (EG) for different amplicons using a Bio-Rad QX-200 system (Bio-Rad, Hercules, Calif.). Our assay utilizes differences in amplicon length for quantitative measurement of multiplexed copy number variation (CNV) or single nucleotide variants (SNVs) in a single well. We designed the region of interest (ROI) variant specific amplicon to be slightly longer that the reference non-variant sequence. The increase in length of the amplicon results in an increase in the base pairs of double-stranded DNA present in a positive droplet. Since the fluorescent amplitude of the EG dye is proportional to the amount of dsDNA present, a droplet with a longer amplicon will fluoresce more brightly than a droplet with a shorter amplicon (FIG. 1). We showed that EvaGreen fluorescence amplitude varies based on amplicon length (FIG. 2) and manipulated this feature to multiplex two targets in one well. Subsequently, we utilized these features to accurately detect and quantify copy number variations (CNVs) such as gene amplifications and SNVs such as mutations from cancer cell lines and patient samples. The sensitivity and specificity of this approach is high, even in the context of genetic mixtures where the genetic variant of interest is represented at only a small fraction of the overall DNA.

Experimental Section

Ethics Statement.

Sample DNA was collected from the Stanford Tissue Bank and approved by the Institutional Review Board (IRB) of Stanford University School of Medicine.

DNA Samples and Processing.

We used human genomic DNA as the template in all digital PCR assays in this study. The control DNA was sourced from a Yoruban individual (NA18507; Coriell Institute, Camden, N.J.). Genomic DNA (NA18507, NA04626, and NA06061) containing varying degrees of X-chromosome aneuploidy were obtained from the Coriell Institute. Patient samples were sourced from colorectal tumor-normal pairs from the Stanford Cancer Institute Tissue Bank. We processed these tumor samples with the E.Z.N.A DNA/RNA/Protein extraction kit (Omega Bio-Tek, Norcross, Ga.) and treated post-extraction samples with RNase A for 1 hour at 37° C. All FLT3 gene amplified colorectal cell lines were extracted from culture using the DNeasy Tissue Kit (Qiagen, Hilden, Germany) following the manufacturer's protocols. Cancer cell line DNA (LS411N, NCIH176, and HT29) was obtained from ATCC (Manassas, Va.) and Dr. Walter Bodmer (Cambridge, UK).

Primer Design and Optimization.

Figure 3A:
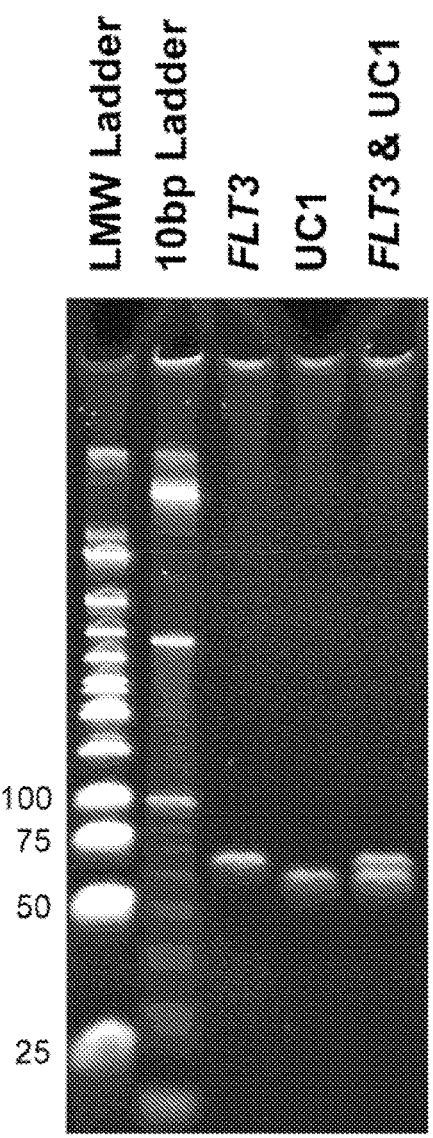
FIGS. 3A and 3B show primer optimization for CNV assays.

For all copy number assays, we designed primers to be around 20 bp in length using Primer3, verified their specificity with UCSC Genome Browser Primer BLAT and purchased from IDT (Integrated DNA Technologies, Coralville, Iowa). Primer sequences are listed in Table 1. For each, we performed simplex PCR using human genomic control DNA, NA18507 (Coriell) and confirmed the presence of the correct products with electrophoresis on a non-denaturing TBE acrylamide gel (FIG. 3A). For all mutation quantification assays, we designed primers and verified specificity using IDT's PrimerQuest (idtdna.com/Primerquest/Home/Index). We designed the complimentary region of primers to be around 20 bp in length with the SNP as the last base pair on the 3' end and melting temperatures within 3° C. of each other. Using NA18507 and LS411N (ATCC), we confirmed the presence of specific bands on a 2% agarose gel and then designed non-complimentary tail sequences of varying lengths to be added to the 5' end. Short tails had high GC content, while long tails were AT rich to maintain melting temperatures within 3° C. of each other.

TABLE 1

Primer sequences

| Gene | Length (bp) | Forward | Reverse |
| --- | --- | --- | --- |
| UC1 | 60 | TGAGGGATTCGGCAGATGTTG (SEQ ID NO: 1) | CTGAAAGGCTGGACTTGACAGA (SEQ ID NO: 2) |
| FLT3 | 66 | GGGATAGGACTCCTGGGTTT (SEQ ID NO: 3) | GTGAGCAGCCTGCATTACCT (SEQ ID NO: 4) |
| FLT3* | 66 | TCAGTGGCAAGAAACGACAC (SEQ ID NO: 5) | AGCTGATTGACTGGGATGCT (SEQ ID NO: 6) |
| FLT3 | 100 | TCAGTGGCAAGAAACGACAC (SEQ ID NO: 7) | GTGAGCAGCCTGCATTACCT (SEQ ID NO: 8) |
| FLT3 | 277 | TCAGTGGCAAGAAACGACAC (SEQ ID NO: 9) | ATTCAAGCGAGCCTGGTTTA (SEQ ID NO: 10) |
| FLT3 | 482 | TCAGTGGCAAGAAACGACAC (SEQ ID NO: 11) | CAGTGCTCACTGCCCTAACA (SEQ ID NO: 12) |
| FLT3 | 592 | TCAGTGGCAAGAAACGACAC (SEQ ID NO: 13) | CATTATGGCTGAACGCTGTG (SEQ ID NO: 14) |
| FLT3 | 740 | TCAGTGGCAAGAAACGACAC (SEQ ID NO: 15) | CAGCACCACTCTTCCATTGAT (SEQ ID NO: 16) |
| FLT3 | 903 | TCAGTGGCAAGAAACGACAC (SEQ ID NO: 17) | CTGCAGGTCAGGTTGGATAAT (SEQ ID NO: 18) |
| G6PD | 64 | GCCAGTGGCAGAGTAAGGAG (SEQ ID NO: 19) | TCTCCTGGGTCTCAGGCTTA (SEQ ID NO: 20) |
| BRAF-WT | 65 | CATGAAGACCTCACAGTAAA (SEQ ID NO: 21) | CCACTCCATCGAGATTTCA (SEQ ID NO: 22) |
| BRAF-MUT | 65 | CATGAAGACCTCACAGTAAA (SEQ ID NO: 23) | CCACTCCATCGAGATTTCT (SEQ ID NO: 24) |

*Used for amplicon length experiment ddPCR Assay Conditions and Optimization.

As the initial step, we treated all of the genomic DNA samples with the restriction enzyme EcoRI for 1-2 hours at 37° C., with subsequent heat-kill at 65° C. for 20 minutes. This restriction enzyme digest ensured that all potentially linked tandem gene copies in our high-quality DNA would be randomly and independently distributed into the droplets.

For all assembled 20 μl PCR reaction mixtures, we included the following: 2× EvaGreen Supermix (Bio-Rad) and primers at a final concentration of 0.1 μM. We loaded 20 ng of NA18507 template DNA into all reactions with the exception of assays examining fluorescence intensity as a function of the amount of template DNA. We partitioned each reaction mixture into approximately 20,000 droplets with a droplet generator (Bio-Rad QX-200), then cycled with the following conditions: 95° C. for 5 minutes (1 cycle); 95° C. for 30 seconds and 52-62° C. for 1 minute (40 cycles); 4° C. for 5 minutes, 90° C. for 5 minutes (1 cycle), 4° C. hold. Cycled droplets were read individually with the QX200 droplet-reader (Bio-Rad).

For optimization of new primer sets, we used an annealing temperature gradient for PCR. Based on this assessment, for the CNV assays we chose an annealing temperature of 60° C. for the FLT3 primers and 61° C. for G6PD primers. For SNV primers, we ran first one annealing temperature gradient for tail-less primers. Subsequently, we employed a temperature gradient for primers with tails using a segmented annealing step as follows: 95° C. for 30 seconds and the optimal annealing temperature for tailless primers for 1 minutes (4 cycles); 95° C. for 30 seconds and 52-62° C. for 1 minute (41 cycles). For the BRAF V600E primers, we used an annealing temperature of 55° C. for 4 cycles and then ramped up to an annealing temperature of 60° C. for 41 cycles.

Clustering Analysis of Droplet PCR.

We exported the fluorescence amplitude of each droplet from the QuantaSoft droplet reader software (Bio-Rad) and, briefly, clustered the droplets into distinct groups using a distance-based minimum-variance linkage algorithm in MATLAB (Mathworks, Natick, Mass.). We eliminated droplets with extreme outlying amplitudes (<0.01% of the total droplets) from the analysis pipeline. We computed the number of negative droplets as if all droplets from three replicate wells were pooled together into one well. The concentration of each target was calculated as follows:

$$\frac{-\ln\left(\frac{\text{negative droplets}}{\text{total droplets}}\right)}{\text{droplet volume}}$$

Droplets intermediate between two cluster populations did not significantly alter the calculated concentration.

For copy number reactions run without replicates, we clustered the droplets and calculated copy number using the QuantaSoft software. The error reported for a single well was the Poisson 95% confidence interval. We used the automated clustering analysis for both FLT3 and G6PD. We calculated copy number as 2× the ratio of ROI concentration versus reference concentration. We calculated the average and standard deviation across triplicates as weighted by the number of detected droplets in each well.

We used the automated clustering analysis for BRAF mutation quantification as described above. Percent mutant was calculated as follows:

$$\left(\frac{[MUT]}{[MUT]+[WT]}\right)\times 100$$

We calculated the average and standard deviation across triplicates as weighted by the number of detected droplets in each well.

Amplicon Length Experiment.

We used the cycling protocol described above, except for longer amplicons (>500 bp) we extended the annealing/extension step to 2 minutes. For this assay we ran only one well per template amount and generated copy numbers and 95% Poisson confidence intervals with the QuantaSoft platform.

Amplified DNA Spike-In Experiments.

We used the cycling protocol for CNV as described above. We reported the copy number for NCIH176 from Cancer Cell Line Encyclopedia microarray data (Barretina et al. (2012) Nature 483(7391):603-607) and from Coriell Institute for NA18507. Dilutions of 1:5, 2:3, 3:2, 5:1 NCIH176 to 18507 were made by volume.

Quantitative SNV Measurements on Controls and Spike-In Experiments.

All expected mutation concentrations from cancer cell lines and control human DNA were derived from ddPCR with the PrimePCR™ BRAF V600E TaqMan assay (Bio-Rad). For these TaqMan control assays we cycled with a single annealing temperature of 55° C. as per manufacturer recommendation. Concentration of mutant was calculated from triplicate using the Bio-Rad QuantaSoft platform. Subsequently, we used the concentrations (copies/µl) derived from the TaqMan assay to create dilutions of LS411N DNA into wild-type Human Male Control (Invitrogen, Carlsbad, Calif.). We examined dilutions of 40%, 30%, 20%, 5%, 1% and 0.5% of mutant copies into wild-type. This assay relied on the same cycling protocol for EG mutation quantification as described previously.

Results and Discussion

We developed single color ddPCR assays to measure two classes of genetic variation; (1) copy number variations and (2) SNVs. As a proof-of-principle, we designed assays to quantify the following: the copy number amplification of the gene FLT3 that is a cancer oncogene and the BRAF V600E mutation that is a frequent mutation in colon cancer and melanoma. To develop these assays, we conducted a number of pilot optimization experiments.

The ability to multiplex two genes in a single-color ddPCR system is contingent on the ability to distinguish between double negative, single positive and double positive droplet clusters (FIG. 1). Differences in the fluorescence amplitude, determined by the amount of EG dye bound, can be used to distinguish these droplet populations. We show that in a singleplex ddPCR reaction, the amplicon length can be used to manipulate the fluorescence of a particular droplet.

Figure 2A:
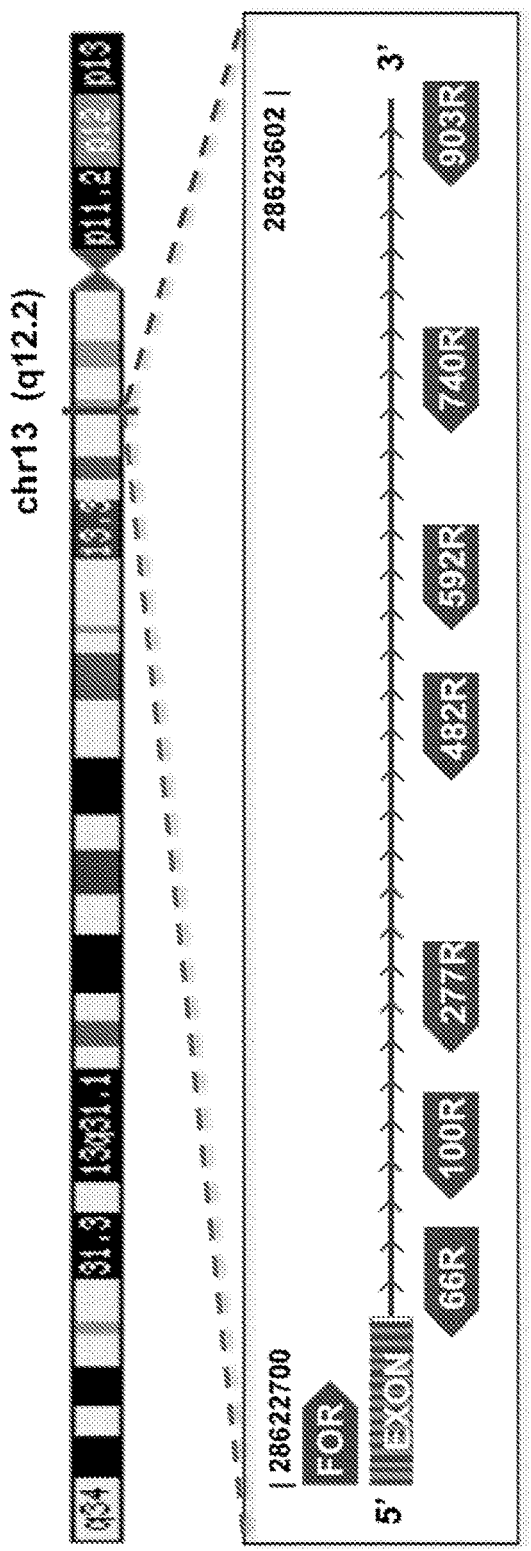
FIGS. 2A and 2B show the effect of amplicon length on EvaGreen fluorescence amplitude.
Figure 2B:
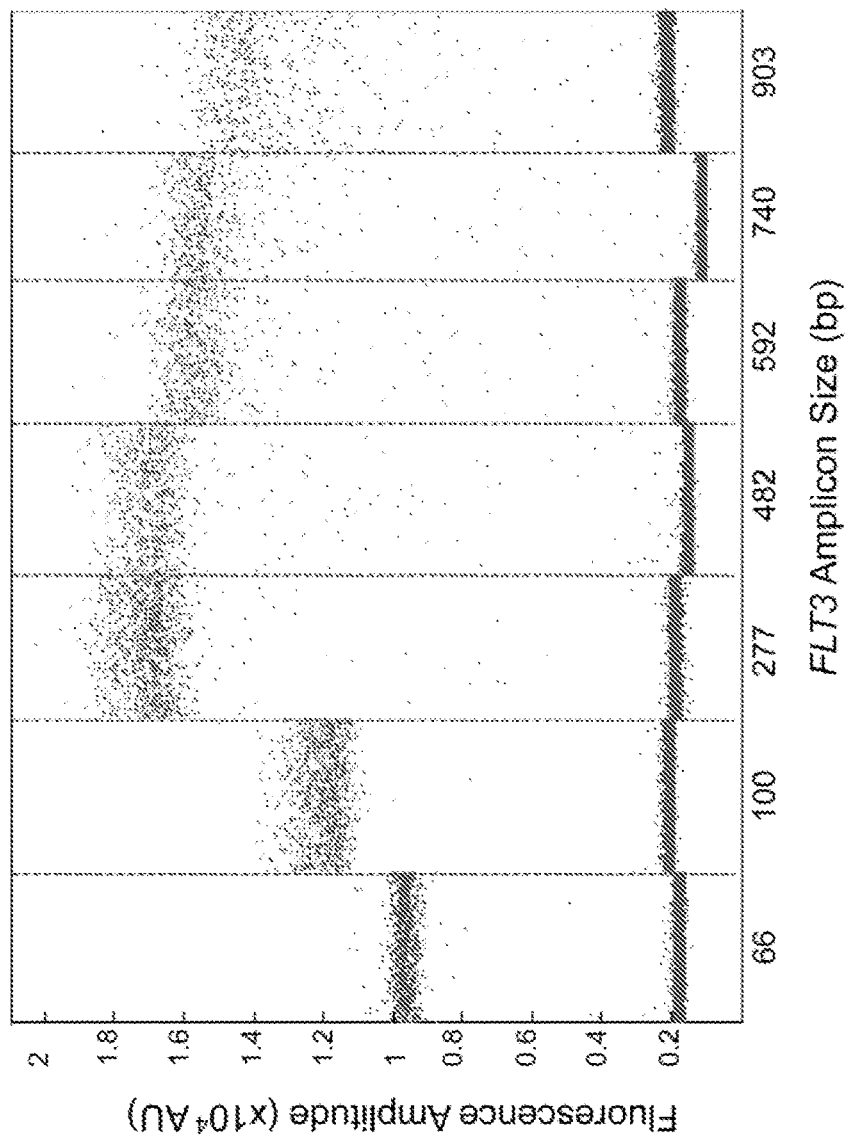

When we increased the amplified length of a FLT3 region, we saw a correlation in increasing fluorescence amplitude with increasing amplicon size up to 500 bp (FIG. 2). With amplicons longer than 500 bp, there was a decrease in positive-droplet fluorescence and an increase in the number of droplets with intermediate fluorescence. This phenomenon implies that amplification of these long regions may be incomplete.

Copy Number Determination.

Figure 3B:
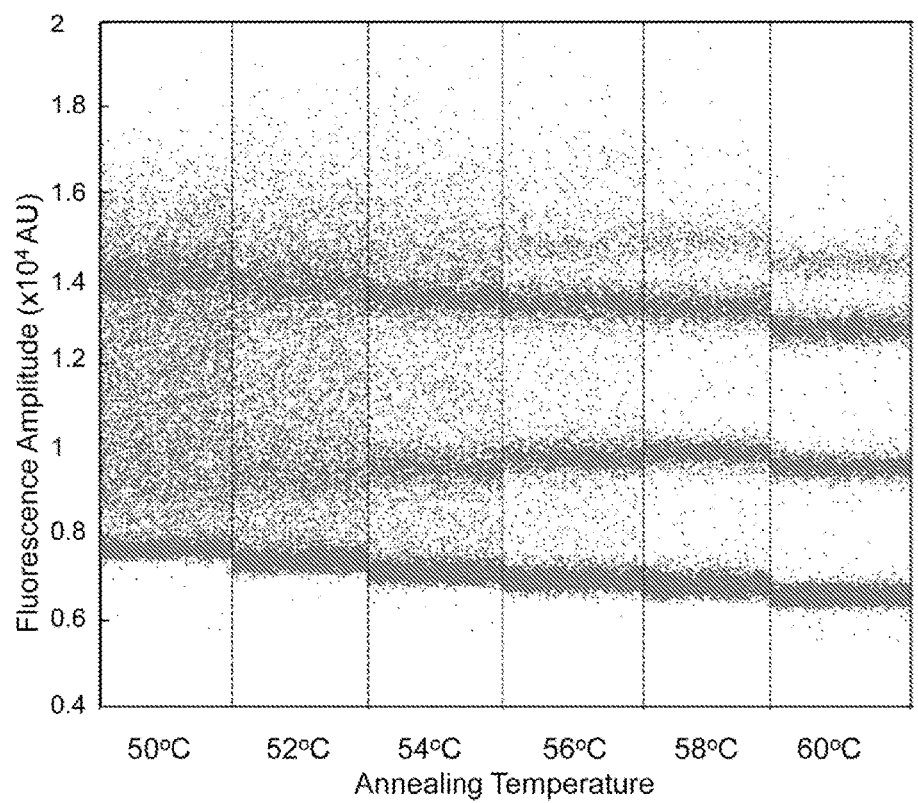

Based on this assessment, we designed a reference target and ROI with differing amplicon lengths in order to assess copy number. We verified the presence of the two correctly sized PCR products by electrophoresis on a non-denaturing acrylamide gel (FIG. 3A). Additionally, we were able to identify four distinct droplet populations corresponding to the presence of one or both of the amplicons (FIG. 3B). We found that across a range of annealing temperatures, 60° C. produced the most distinct droplet population separation for the FLT3-UC1 gene pair. The disparity in droplet population across temperatures indicates that the multiplexed nature of this assay is largely dependent upon the amplification efficiency of the ddPCR reaction. This aspect must be considered when designing primers to multiplex in an EG ddPCR system.

Figure 6:
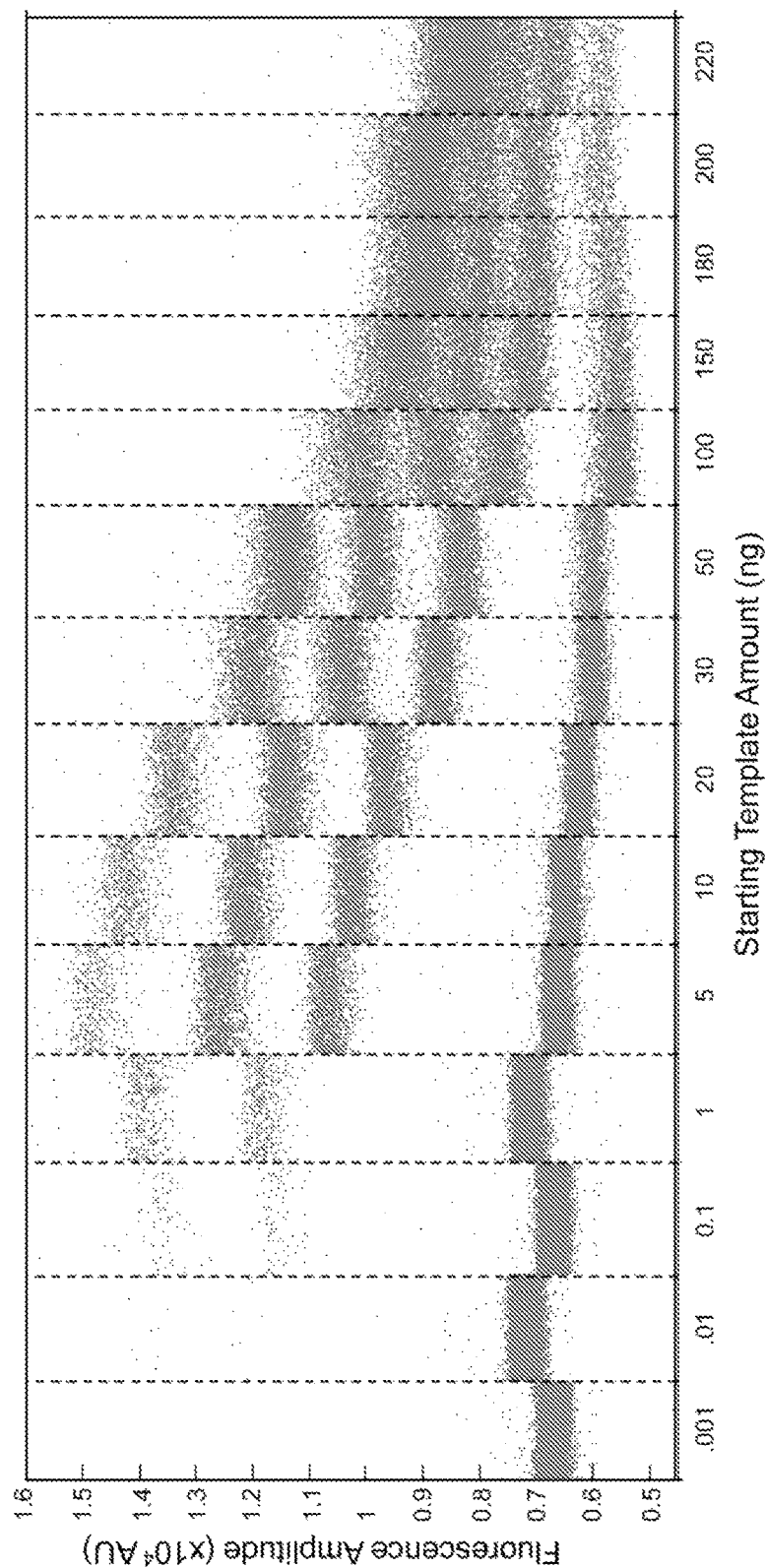
FIG. 6. shows the effect of starting template amount on fluorescence amplitude. Each column is one multiplexed reaction with UC1 and FLT3 primers (~20,000 droplets). Starting template amount refers to the high-quality NA18507 loaded into each 20 µl PCR reaction.

The amount of starting template DNA added per reaction can also affect the degree of droplet population separation. Due to the nonspecific binding fluorescence of the EG dye, the background signal of the unamplified product in the negative droplets increases with the amount of template DNA loaded. Also, the difference in fluorescence between negative and positive droplets accordingly shrinks. With starting template concentrations ranging from 0.25 ng/µl to 2.5 ng/µl, we found that there was a clear amplitude separation between the droplet clusters (FIG. 6). Although the populations were significantly condensed at higher concentrations, we were still able to accurately cluster droplets with a final DNA template concentration up to 10 ng/µl. Because the ROI and reference amplicons make up an extremely small fraction of the total human genome size, we are still in the Poisson dilution threshold for digital PCR. Additionally, we found that as little as 1 ng of high-quality DNA (NA18507) in a 20 µl reaction was required to yield the expected 2.02 copy number (Poisson 95% confidence interval=0.42).

Regardless of the concentration of initial template, our human control DNA sample had a FLT3 copy number reproducibly close to two. This is the expected result for a normal diploid genome, reflective of a one-to-one ratio between the number of FLT3 positive droplets and UC1 positive droplets (FIG. 6). When choosing a reference gene, we wanted to confirm that disparities in primer efficiency between UC1 and FLT3 did not significantly contribute to fluorescent amplitude. Along these lines, if the primer efficiency is not the same, we might expect that a less efficient primer pair would produce lower amplicon droplets. In that case we would also expect the number of positive droplets in the lower amplitude population to be less. However, because there was no difference in the number of UC1 positive droplets versus FLT3 positive droplets, we are confident that primer efficiency does not play a major role in determining fluorescent amplitude in our assay.

Figure 4A:
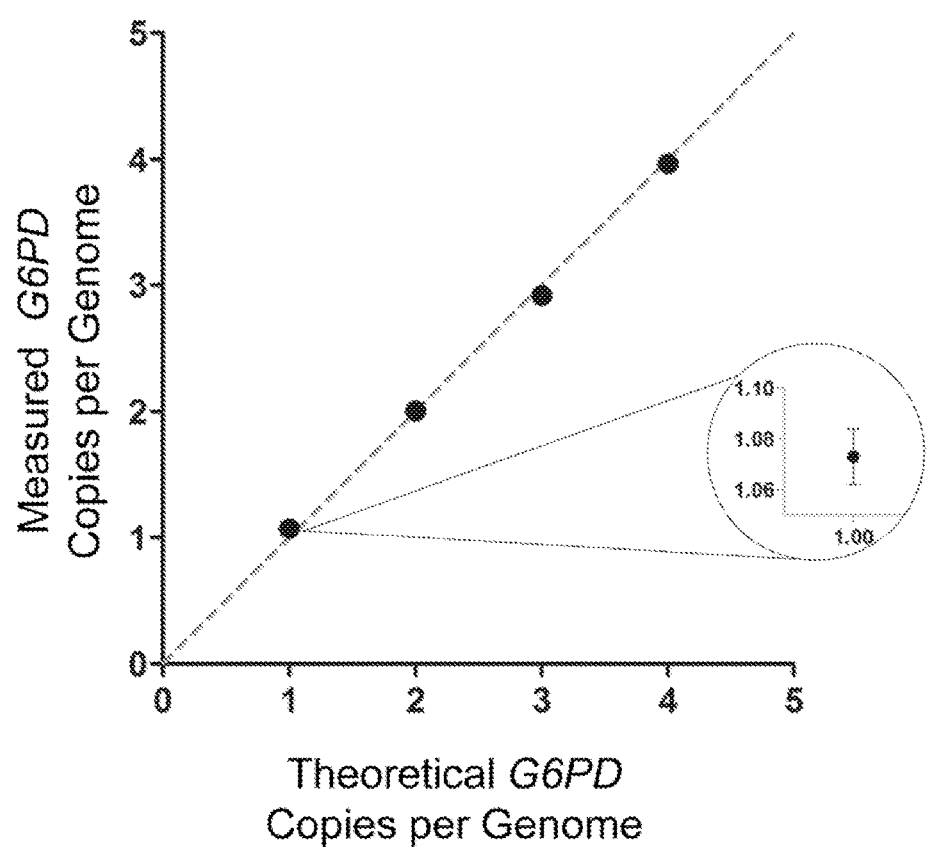
FIGS. 4A and 4B show sensitivity testing of EvaGreen CNV assays on control DNA. FIG. A shows G6PD copy number measured in four human X-chromosome disorder DNA samples (Coriell). The expected one-to-one line (light gray) is based on the copy numbers provided by the Coriell Institute.

We explored the accuracy of our assay in detect integer level CNV by analyzing the number of copies of the X-linked gene, G6PD, in DNA samples from patients with known X-chromosome aneuploidy. We accurately distinguished between G6PD copy numbers ranging from 1 to 4 at close to integer values (FIG. 4A). This indicates the ability of the assay to not only evaluate copy number amplification, but also offer an accurate metric for detecting gene deletions. The standard deviations of copy numbers detected varied in the one hundredth to thousandth of a copy, indicating a highly reproducible method with research and diagnostic potential to detect germline CNV.

Figure 4B:
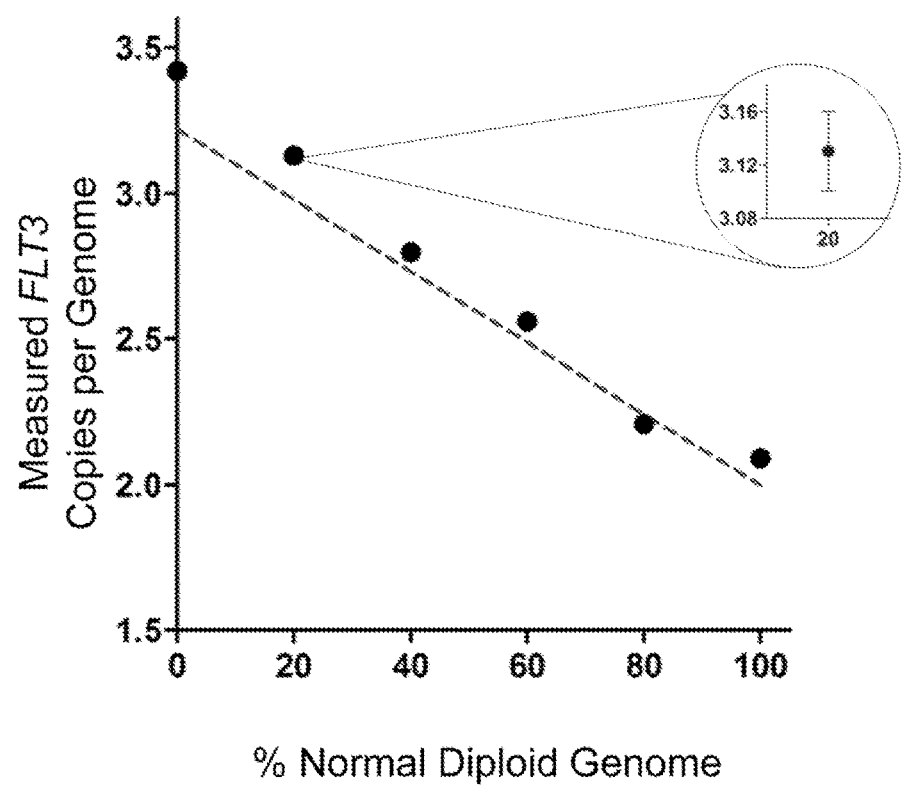

While all of our DNA samples yielded near integer copy number values, this is not always the case in cancer samples (Table 2). Most clinical tumor samples are a mixture of normal and tumor cells at varying percentages, as well as genetically dissimilar sub-clones of cancer cells. To assess the sensitivity of our system in detecting heterogeneous tumor samples, we measure FLT3 copy number in an amplified cell line (NCIH176) diluted into normal diploid DNA (NA18507). NCIH176 has a tumor cell line a FLT3 amplified copy number of around 3.5 copies per genome. We found that our method had the sensitivity to detect a tumor sample diluted 1:4 in normal template (FIG. 4B). The performance of the assay on mixed samples indicates robust copy number evaluation in cancer samples that are tumor and normal cell mixtures.

TABLE 2

FLT3 Copy number of colorectal patient samples

| Template | Source | EvaGreen Copy Number | StDev |
|---|---|---|---|
| 18507 | normal diploid DNA | 2.051 | 0.005 |
| 1668 | patient tumor | 3.089 | 0.025 |
| 1480 | patient tumor | 2.644 | 0.003 |
| 825 | patient tumor | 1.996 | 0.007 |
| 1563 | patient tumor | 1.530 | 0.007 |

Quantitative Detection of Single Nucleotide Variants.

Figure 5A:
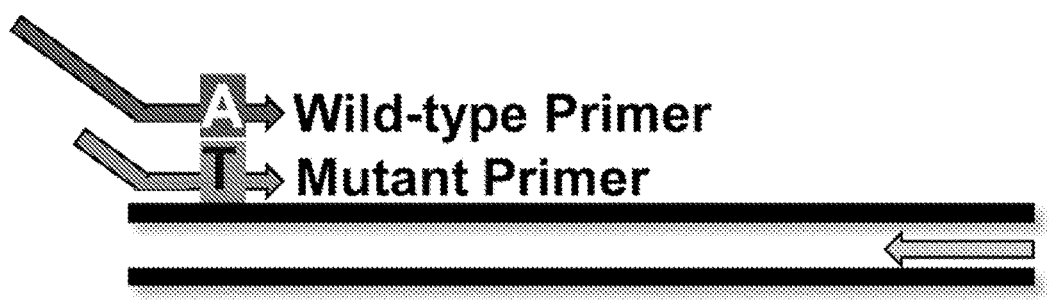
FIGS. 5A-5F show one-color SNV quantification.

In addition to copy number assessment, we designed an assay for the BRAF V600E point mutation using the same concept of amplicon length variation to separate droplet populations. The design incorporated a long, non-complementary tail (AAATAAATAAATAAATAAATAAATAAATAAATAAATAAA, SEQ ID NO:25) onto the 5' end of the BRAF wild-type primer and a short tail (GGGGGG) onto the BRAF mutant primer. The longer amplicon produced higher amplitude positive droplets than the shorter amplicon, thus the population of wild-type positive droplets and mutant positive droplets were able to be clustered and quantified similar to the CNV assay (FIG. 5A).

We tested this primer mix on a series of diploid control DNA, cancer cell lines and a colorectal patient sample for which next-generation sequencing had verified the presence of the targeted mutation. In all cases, we compared our method of multiplexing with EG to BioRad's commercially available PrimePCR BRAF V600E assay, which utilizes TaqMan chemistry. In BioRad's assay a FAM probe hybridizes to the mutant sequence and a HEX probe hybridizes to the wild-type sequence, so each are read as separate clusters on two distinct channels. The EG reported values were similar to the values generated from Bio-Rad's commercially available PrimePCR BRAF V600E assay, which utilizes TaqMan chemistry. The concentrations (copies/µl) of mutant and wild-type measured with PrimePCR for each of the control samples were used as a reference throughout our study. The EG measured values for the controls were universally similar to these reference values (Table 3).

TABLE 3

Comparison between EvaGreen and TaqMan mutation quantification methods on control template DNA.

| Template | Source | %Mutant Evagreen | TaqMan |
|---|---|---|---|
| 18507 | normal diploid DNA | 0.01 | 0.00 |
| Human Male Control | normal diploid DNA | 0.00 | 0.00 |
| HT29 | cancer cell line | 25.38 | 25.68 |
| LS411N | cancer cell line | 67.48 | 66.36 |
| 168B | patient-benign | 0.00 | 0.00 |
| 168M | patient-malignant | 25.30 | 27.13 |

Figure 5B:
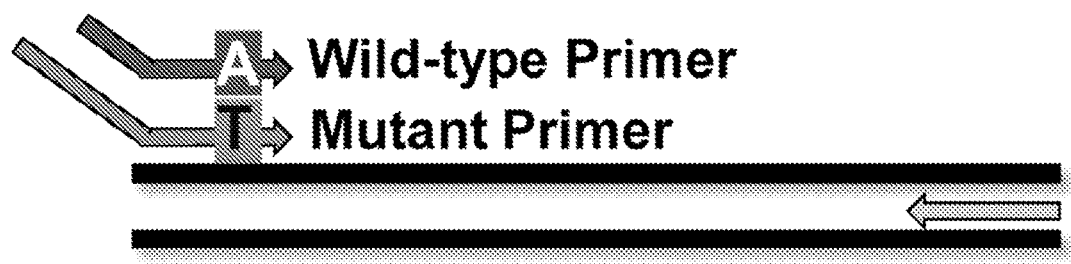
Figure 5C:
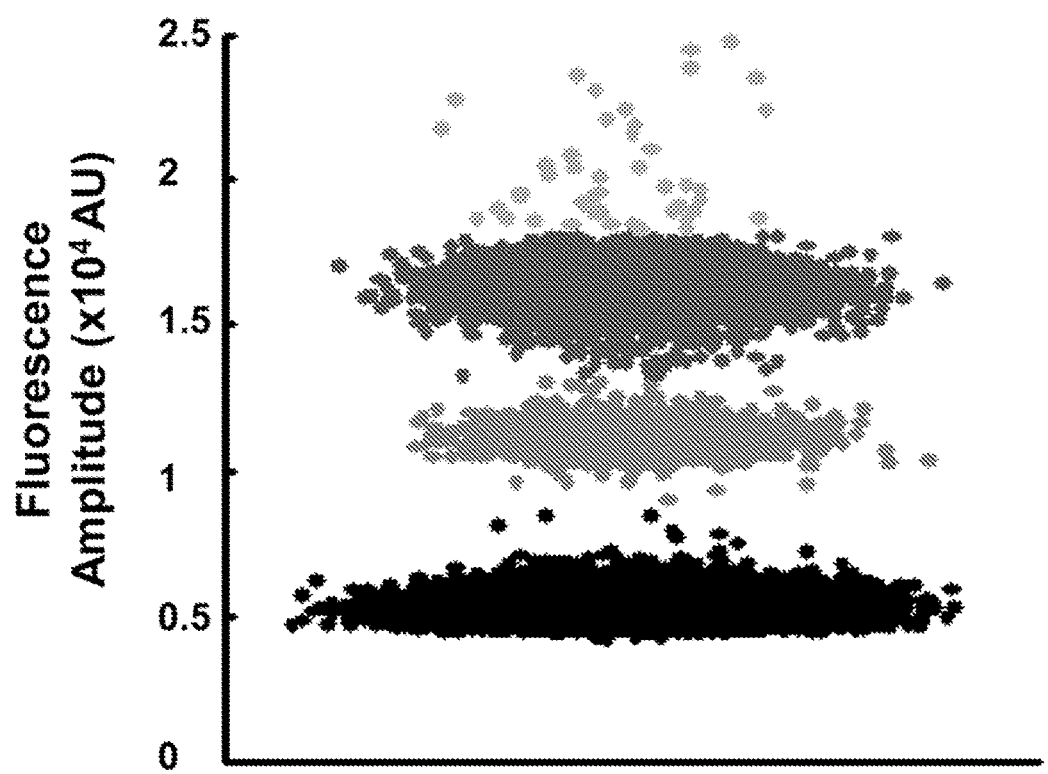

To further test the accuracy of our assay in comparison to its TaqMan counterpart, we used our BRAF tail assay to amplify a known template mixture (80% wild-type template and 20% mutant template). Three populations were easily distinguishable and we measured the ratio of mutant to wild-type as 0.24 (FIG. 5B). Next, we engineered a "swap" so that the wild-type primer was designed with the short tail and the mutant primer with the long tail. Using the same template mixture (4:1) we measured the ratio of wild-type template to mutant as 0.26 (FIG. 5C). The close correspondence of these results to the genotype representation indicates amplicon length as the primary factor in determining population amplitude.

Figure 5D:
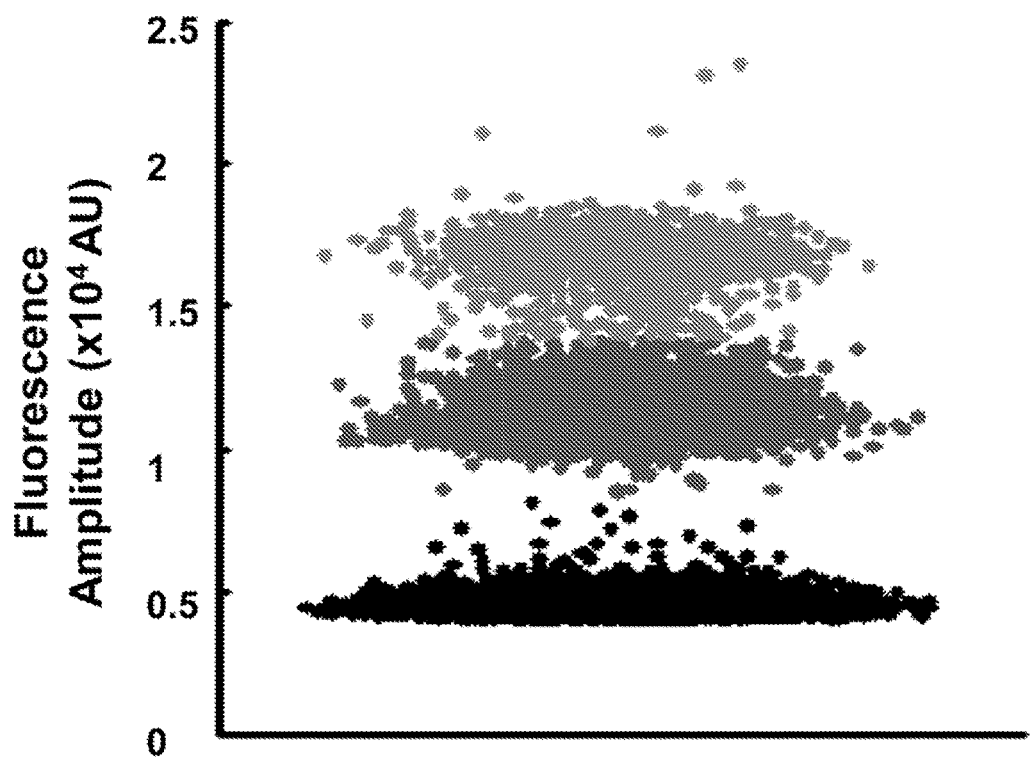
Figure 5E:
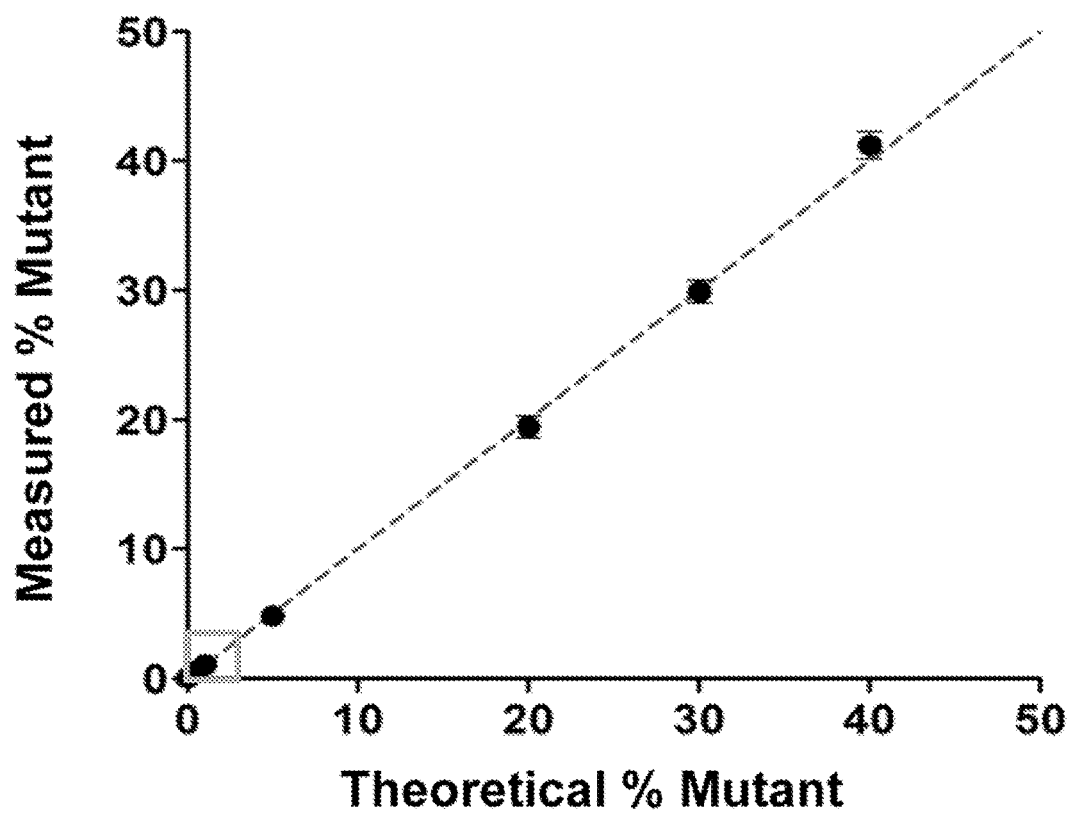
Figure 5F:
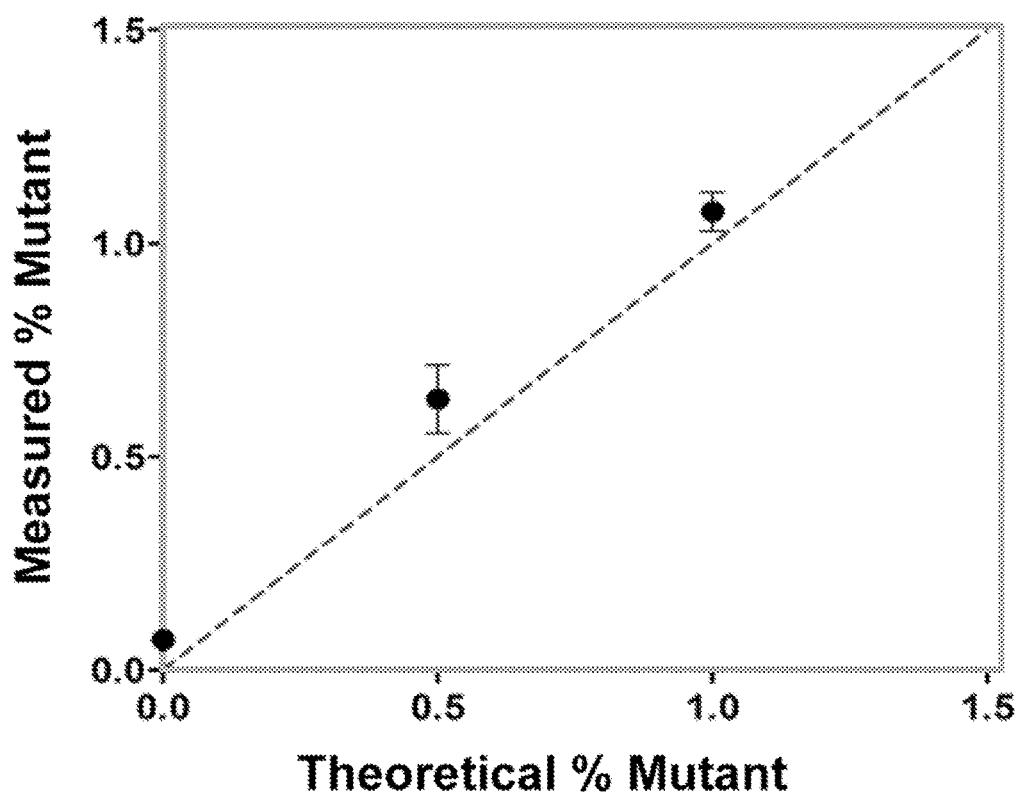

Finally, we measured the sensitivity of our mutation detection assay by performing a dilution of mutation template into increasing amounts of wild-type genomic DNA lacking the mutation (FIG. 5D). Even at an expected mutation concentration of less than 1%, the single color assay could accurately quantify the mutant (FIG. 5E). This has implications for the use of this method in detecting rare nucleotide variants, as well as mutation detection in low concentration samples such as circulating nucleic acids.

CONCLUSION

We demonstrated the multiplexed quantification of nucleic acids in a one-color digital PCR format by exploiting the shift in fluorescence amplitude due to varying amplicon size. This method retains the accuracy found in TaqMan-based droplet digital PCR platforms while eliminating the need for optimization of the probe oligonucleotide. Sampling error is minimized because both the ROI and the reference gene are measured from the same template. We showed that this single-color ddPCR strategy is robust in analyzing germline copy number variations, as well as quantifying copy number variation in admixtures between tumor and normal DNA. Through the direct manipulation of amplicon size using 5' primer tails, we were also able to detect and quantify single nucleotide mutations at very low concentrations.

Since a third oligonucleotide is unnecessary in this system, it is possible to use shorter amplicons, which is preferable in the context of degraded DNA. Whereas TaqMan-based assays are limited by the efficiency of the oligonucleotide probe and dependent on the neighboring nucleotide context, our single-color digital PCR strategy is a flexible platform that can be used to interrogate a wide range of targets.

Although preferred embodiments of the subject invention have been described in some detail, it is understood that obvious variations can be made without departing from the spirit and the scope of the invention as defined herein.

What is claimed is:

1. A method for determining the relative copy number of a target polynucleotide sequence in a genome of a subject, the method comprising:
   a) collecting a biological sample comprising nucleic acids from the subject;
   b) dividing the nucleic acids of the biological sample into a plurality of partitions;
   c) amplifying the nucleic acids by digital PCR using:
      i) a first set of primers for amplification of a region of interest in the target polynucleotide sequence, wherein each primer comprises a first 5'-tail of a first length,
      ii) a second set of primers for amplification of a reference polynucleotide sequence present in at least one of the nucleic acids of the biological sample, wherein each primer comprises a second 5'-tail of a second length, wherein the shorter of the two 5'-tails has a higher GC content, and the longer of the two 5'-tails has a higher AT content such that the melting temperature for primer-template hybridization complexes for the target and reference polynucleotides are within 3° C. of each other, wherein the size of the amplicons produced for the target polynucleotide sequence and the reference polynucleotide sequence differ in length, and
      iii) a fluorescent DNA dye;
   d) measuring the fluorescence signal from each partition after amplification in order to determine the presence or absence of amplicons for the region of interest and the reference polynucleotide sequence; and
   e) summing the results over all the partitions to determine the relative copy number of the target polynucleotide sequence compared to the reference polynucleotide sequence.

2. The method of claim 1, wherein the target polynucleotide sequence is a sequence for which deletion or duplication is associated with a phenotype of interest.

3. The method of claim 2, wherein 1, 2, 3, 4, 5, or 6 copies of the target polynucleotide sequence are present in the genome of the subject.

4. The method of claim 1, wherein at least one primer of the first set of primers hybridizes to a coding region of the target polynucleotide.

5. The method of claim 1, wherein at least one primer of the first set of primers hybridizes to a non-coding region of the target polynucleotide.

6. The method of claim 1, wherein the biological sample is from an animal, plant, bacterium, fungus, or protist.

7. The method of claim 1, wherein the biological sample comprises a genetically aberrant cell, rare blood cell, or cancerous cell.

8. The method of claim 1, wherein digital PCR is performed in a microfluidic device.

9. The method of claim 1, further comprising isolating at least one target polynucleotide from the biological sample.

10. The method of claim 1, wherein the 5'-tail of the first length is shorter and has a higher GC content than the 5'-tail of the second length such that the melting temperature for the primer-template complexes for the target and reference polynucleotides are within 3° C. of each other.

11. The method of claim 10, wherein the 5'-tail of the second length comprises the nucleotide sequence of SEQ ID NO:25.

12. The method of claim 1, wherein the 5'-tail of the first length is longer and has a higher AT content than the 5'-tail of the second length and has a higher AT content such that the melting temperature for primer-template hybridization complexes for the target and reference polynucleotides are within 3° C. of each other.

13. A method for detecting and quantifying a mutation in a target polynucleotide sequence in a genome of a subject, the method comprising:
   a) collecting a biological sample comprising nucleic acids from the subject;
   b) dividing the nucleic acids of the biological sample into a plurality of partitions;
   c) amplifying the nucleic acids by digital PCR to produce an amplicon of the region of interest comprising the mutation using:
      i) a first set of primers for amplification of the region of interest comprising the mutation in the target polynucleotide sequence, wherein each primer comprises a first 5'-tail of a first length,
      ii) a second set of primers for amplification of a reference polynucleotide sequence comprising a non-variant reference sequence for the target polynucleotide, said reference polynucleotide sequence being present in at least one of the nucleic acids of the biological sample, wherein each primer comprises a second 5'-tail of a second length, wherein the shorter of the two 5'-tails has a higher GC content, and the longer of the two 5'-tails has a higher AT content such that the melting temperature for primer-template hybridization complexes for the target and non-variant reference polynucleotides are within 3° C. of each other, wherein the amplicon of the region of interest differs in length from an amplicon of the reference polynucleotide sequence comprising the non-variant reference sequence for the target polynucleotide, and
      iii) a fluorescent DNA dye;
   d) measuring the fluorescence signal from each partition after amplification in order to determine the presence or absence of amplicons for the region of interest and the non-variant reference sequence; and e) summing the results over all the partitions to determine the relative amount of the mutation in the genome of the subject compared to the non-variant reference sequence.

14. The method of claim 13, wherein the mutation is an insertion, a deletion, or a replacement.

15. The method of claim 14, wherein the mutation is a single nucleotide variation.

16. The method of claim 13, wherein the mutation is associated with a phenotype of interest.

17. The method of claim 13, wherein the biological sample is from an animal, plant, bacterium, fungus, or protist.

18. The method of claim 13, wherein the biological sample comprises a genetically aberrant cell, cancer cell, or rare blood cell.

19. The method of claim 13, wherein digital PCR is performed in a microfluidic device.

20. The method of claim 13, further comprising isolating at least one target polynucleotide from the biological sample.

21. The method of claim 13, wherein the mutation is a common genetic variant or a rare genetic variant.

22. The method of claim 13, wherein the 5'-tail of the first length is shorter and has a higher GC content than the 5'-tail of the second length such that the melting temperature for the primer-template complexes for the target and reference polynucleotides are within 3° C. of each other.

23. The method of claim 22, wherein the 5'-tail of the second length comprises the nucleotide sequence of SEQ ID NO:25.

24. The method of claim 13, wherein the 5'-tail of the first length is longer and has a higher AT content than the 5'-tail of the second length such that the melting temperature for primer-template hybridization complexes for the target and non-variant reference polynucleotides are within 3° C. of each other.

25. The method of claim 13, wherein the relative amount of the mutation in the genome is less than 1% of the amount of the non-variant reference sequence.

* * * * *